US008039642B2

(12) United States Patent
Liu et al.

(10) Patent No.: US 8,039,642 B2
(45) Date of Patent: Oct. 18, 2011

(54) PYRENYLOXYSULFONIC ACID FLUORESCENT AGENTS

(75) Inventors: Jixiang Liu, Eugene, OR (US); Richard Haugland, Olympia, WA (US); Wai-Yee Leung, San Ramon, CA (US)

(73) Assignee: Life Technologies Corporation, Carlsbad, CA (US)

( * ) Notice: Subject to any disclaimer, the term of this patent is extended or adjusted under 35 U.S.C. 154(b) by 753 days.

(21) Appl. No.: 11/871,596

(22) Filed: Oct. 12, 2007

(65) Prior Publication Data

US 2008/0032379 A1 Feb. 7, 2008

Related U.S. Application Data

(63) Continuation of application No. 10/731,987, filed on Dec. 9, 2003, now abandoned.

(51) Int. Cl.
*C07D 207/06* (2006.01)
*C07D 255/02* (2006.01)
(52) U.S. Cl. ........................................ 548/528; 558/410
(58) Field of Classification Search .................. 548/528; 558/410
See application file for complete search history.

(56) References Cited

U.S. PATENT DOCUMENTS

| | | | |
|---|---|---|---|
| 3,996,345 | A | 12/1976 | Ullman et al. |
| 4,374,120 | A | 2/1983 | Soini |
| 4,420,568 | A | 12/1983 | Wang et al. |
| 4,510,251 | A | 4/1985 | Kirkemo et al. |
| 4,542,104 | A | 9/1985 | Stryer et al. |
| 4,711,955 | A | 12/1987 | Ward et al. |
| 4,997,928 | A | 3/1991 | Hobbs |
| 5,047,519 | A | 9/1991 | Hobbs et al. |
| 5,049,673 | A | 9/1991 | Tsien et al. |
| 5,132,432 | A * | 7/1992 | Haugland et al. ............. 548/518 |
| 5,171,534 | A | 12/1992 | Smith et al. |
| 5,208,148 | A | 5/1993 | Haugland et al. |
| 5,332,666 | A | 7/1994 | Prober |
| 5,362,628 | A | 11/1994 | Haugland et al. |
| 5,405,975 | A | 4/1995 | Kuhn et al. |
| 5,453,517 | A | 9/1995 | Kuhn et al. |
| 5,459,268 | A | 10/1995 | Haugland et al. |
| 5,576,424 | A | 11/1996 | Mao et al. |
| 5,648,270 | A | 7/1997 | Kuhn et al. |
| 5,686,261 | A | 11/1997 | Zhang et al. |
| 5,714,327 | A | 2/1998 | Houthoff et al. |

FOREIGN PATENT DOCUMENTS

| WO | WO-94/05688 | 3/1994 |
|---|---|---|
| WO | WO-2005/064336 | 7/2005 |

OTHER PUBLICATIONS

U.S. Appl. No. 10/731,987, "Amendment/Req. Reconsideration after Non-final Rejection filed", Mar. 3, 2007.
U.S. Appl. No. 10/731,987, "Final Office Action mailed", May 24, 2007.
U.S. Appl. No. 10/731,987, "Non-final Office Action mailed", Aug. 23, 2006.
U.S. Appl. No. 10/731,987, "Response to Non-final Office Action filed", Nov. 22, 2006.
U.S. Appl. No. 10/731,987, "Response to Restriction Requirement filed", Jun. 9, 2006.
U.S. Appl. No. 10/731,987, "Restriction Requirement mailed", May 9, 2006.
Baker, Wilson et al., "Fluorescent Acylating Agents derived from 7-Hydroxycoumarin", 1949, S12-S-15.
Barzilay, M. et al., "Anion transport in red blood cells .I. Chemical properties of anion recognition sites as revealed by structure-activity relationships of aromatic sulfonic acids", *Membr Biochem* vol. 2, No. 2 1979, 227-54.
Berge, Stephen M. et al., "Pharmaceutical Salts", *Journal of Pharmaceutical Science* vol. 66 1977, 1-19.
Bouizar, Zhor et al., "Purification and Characterization of Calcitonin Receptors in Rat Kidney Membranes by Covalent Cross-Linking Techniques.", *Eur. J. Biochem*, vol. 155, No. 1 1986, 141-147.
Braunitzer,G. et al., "On epsilon-labelling of peptides: automatic sequence analysis of insulin", *Hoppe Seylers Z Physiol Chem* 354(12)(author's transl.) 1973, 1563-6.
Braunitzer, G. et al., "Variants of haeme complex: the amino acid residues in position E7, E11 and F8 of an insect haemoglobin (erythrocruorin)", *Hoppe Seylers Z Physiol Chem* vol. 352, No. 5 1971, 757-8.
Brinkley, Michael, "A Brief Survey of Methods for Preparing Protein Conjugates with Dyes, Haptens, and Cross-Linking Reagents", *Bioconjugate Chem.*, vol. 3 1992, 2-13.
Browning, Jeffrey et al., "Studies on the Differing Effects of the Tumor Necrosis Factor and Lymphotoxin on the Growth of Several Human Tumor Lines", *J. Immunol.*, vol. 143, No. 6 1989, 1859-1867.
Cornelisse, C. J. et al., "A new type of two-color fluorescence staining for cytology specimens", *J Histochem Cytochem* 24 (1) 1976, 73-81.
Furniss, Brian S. et al., "Resolution of Racemates", *Vogel's Textbook of Practical Organic Chemistry* Fifth Ed, Longman Group UK Ltd., Essex 1989, 809-823.
Greene, T. W., "Protective Groups in Organic Synthesis", *John Wiley & Sons* 2nd Ed. 1991.
Haugland, Richard P., "Molecular Probes Handbook of Fluorescent Probes and Research Chemicals", *Sets 1-7* Molecular Probes, Inc. 1992, 9-41.
Heidelberg, J. F. et al., "DNA sequence of both chromosomes of the cholera pathogen Vibiro cholerae", *Nature* vol. 406, No. 6795 2000, 477-83.
Helgason, Erlendur et al., "Bacillus anthracis , Bacillus cereus, and Bacillus thuringiensis —One Species on the Basis of Genetic Evidence.", *Appl. Envir. Microbiol.* vol. 66 2000, 2627-2630.
Heller, A., "Electrical Wiring of Redox Enzymes", *Acc. Chem. Res.* vol. 23, No. 5 1990, 128-134.
Hemmila, Ilkka, "Fluoroimmunoassays and immunofluorometric assays", *Clin. Chem.* vol. 31 1985, 359.

(Continued)

*Primary Examiner* — James O Wilson
*Assistant Examiner* — Ebenezer O Sackey
(74) *Attorney, Agent, or Firm* — Life Technologies Corporation; Joseph Taffy

(57) ABSTRACT

The invention provides a novel class of reactive fluorescent agents that are based on a pyrene sulfonic acid nucleus. The agents are readily incorporated into conjugates with other species by reacting the reactive group with a group of complementary reactivity on the other species of the conjugate. Also provided are methods of using the compounds of the invention to detect and/or quantify an analyte in a sample. In an exemplary embodiment, the invention provides multi-color assays incorporating the compounds of the invention.

3 Claims, 4 Drawing Sheets

OTHER PUBLICATIONS

Jiang, Sunny C. et al., "Genetic diversity of clinical and environmental isolates of Vibrio cholerae determined by amplified fragment length polymorphism (AFLP).", *Appl. Envir. Microbiol.* 66 2000, 148-153.

Jolley, Michael E. et al., "Flourescence polarization immunoassay I. Monitoring aminoglycoside antibiotics in serum and plasma.", *Clin. Chem.* vol. 27 1981, 1190-1197.

Joshi, Saroj et al., "ATP Synthase Complex from Bovine Heart Mitochondria", *J. Biol. Chem.*, vol. 265, No. 24 1990, 14518-14525.

Jung, Stephanie M. et al., "Crosslinking of platelet glycoprotein Ib by N-succinimidyl(4-azidophenyldithio)propionate and 3,3'-dithiobis-(sulfosuccinimidyl propionate)", *Biochimica et Biophysica Acta*, vol. 761, Iss. 2 1983, 152-162.

Kanaoka, Yuichi, "Organic fluorescence. reagents. In the study. of. enzymes and proteins.", *Angewandte Chemie International Edition* vol. 16 1977, 137-47.

Khalaf, H. et al., ""[5-Isothiocyanato-1, 8-naphthalenedicarbox-4-methylphenylimide, a new fluorescence reagent for compounds containing amino groups (author's transl)]"*Hoppe Seylers Z Physiol Chem* 358(4) 1977, 505-11.

Khalfan, H. et al., ""Aminomethyl coumarin acetic acid: a new fluorescent labelling agent for proteins"", *Histochem J* 18(9) 1986, 497-9.

Khalfan, H. et al., ""Fluorigenic method for the assay of proteinase activity with the use of 4-methylumbelliferyl-casein"", *Biochem J* 209(1) 1983, 265-267.

Kostrikis, L. G. et al., "Spectral Genotyping of Human Alleles", *Science* 279:, American Association for the Advancement of Science 1998, 1228-1229.

Lee, L. G. et al., "Seven-Color, Homogeneous Detection of Six PCR Products.", *BioTechniques* 27, 1999, 342-349.

Malencik, D. A. et al., "Fluorescence polarization studies of the self-association of beef liver glutamate dehydrogenase", *Biochemistry* vol. 11, No. 16 1972, 3022-7.

Park, Linda S. et al., "Characterization of the Cell Surface Receptor for a Multi-Lineage Colony-Stimulating Factor (CSF-2alpha)*", *J. Biol. Chem.*, vol. 261, No. 1 1986, 205-210.

Raju, B. et al., "A fluorescent indicator for measuring cytosolic free magnesium", *Am. J. Physiol.* vol. 256 1989 , C540-C548.

Rinderknecht, H. , ""A new technique for the fluorescent labelling of proteins"", *Experientia* 16 1960, 430-1.

Sandler, Stanley R. et al., "Organic Functional Group Preparations: vol. 3", Academic Press, San Diego 1989, 1-552.

Spatola, Arno F. et al., "Ch 5: Peptide Backbone Modifications: A Structure—Activity Analysis of Peptides Containing Amide Bond Surrogates, Conformational Constraints, and Rela", *Chemistry and Biochemistry of Amino Acids, Peptides and Proteins*, vol. 7 1983, 267-357.

Speth, M. et al., "On the nature of the interaction between 4,4'-diisothiocyanostilbene 2,2'-disulfonic acid and microsomal glucose-6-phosphatase. Evidence for the involvement of sulfhydryl groups of the phosphohydrolase", *European Journal of Biochemistry* vol. 174, No. 1 1988, 111-7.

Staines, W. A. et al., ""Three-color immunofluorescence histochemistry allowing triple labeling within a single section"", *J Histochem Cytochem* 36 (2) 1988, 145-51.

Tyagi, Sanjay et al., "Multicolor molecular beacons for allele discrimination", *Nature Biotechnology*, vol. 16 1998, 49-53.

Weber, Gregorio, "Polarization of fluorescence of macromolecules .I. Theory and eperimental method", *Biochemical Journal* vol. 51, No. 2 1952, 145-155.

Wolfbeis, O. S., ""Acid-Base Titrations Using Fluorescent Indicators and Fiber Optical Light Guides"", *Fresenius Z Anal Chem* 320 1985, 271-273.

Zarling, David A. et al., "Mapping of Lymphocyte Surface Polypeptide Antigens by Chemical Cross-Linking with BSOCOES", *Journal of Immunology*, vol. 124, No. 2 1980, 913-920.

\* cited by examiner

PYRENYLOXYSULFONIC ACID FLUORESCENT AGENTS

CROSS-REFERENCE TO RELATED APPLICATIONS

This application is a continuation of U.S. patent application Ser. No. 10/731,987, filed Dec. 9, 2003, which disclosure is herein incorporated by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention relates to novel fluorescent compounds that have utility in detecting one or more selected analytes in a sample. The invention is of use in a variety of fields including immunology, diagnostics, molecular biology and fluorescence based assays.

BACKGROUND OF THE INVENTION

Fluorescent dyes are widely used as tracers for localization of biological structures by fluorescence microscopy, for quantification of analytes by fluorescence immunoassay, for flow cytometric analysis of cells, for measurement of physiological state of cells and other applications (Kanaoka, *Angew. Chem. Intl. Ed. Engl.* 16: 137 (1977); Hemmila, *Clin. Chem.* 31: 359 (1985)). Among the advantages of fluorescent agent over other types of absorption dyes include the delectability of emission at a wavelength distinct from the excitation, the orders of magnitude greater detectability of fluorescence emission over light absorption, the generally low level of fluorescence background in most biological samples and the measurable intrinsic spectral properties of fluorescence polarization (Jolley et al., *Clin. Chem.* 27: 1190 (1981)), lifetime (U.S. Pat. No. 4,374,120) and excited state energy transfer (U.S. Pat. Nos. 3,996,345; and 4,542,104).

Fluorescent agents are now widely used to determine physiological functions in patients during routine checkups or diagnostic procedures, to monitor the exposure of workers and others to potentially harmful chemicals such as toxic or carcinogenic pesticides or inorganic materials in the atmosphere, soil, or drinking water, in determining the effectiveness of pharmaceuticals on disease states or conditions, in screening new compounds for biological activity as either promoters or inhibitors of particular enzymes, in monitoring gene and transgene expression, and in performing immunological and other laboratory assays such as enzyme-linked immunosorbent assays (ELISAs) and Western blots.

Optical methods of detection, such as fluorescence emission, UV absorptivity, and colorimetry are convenient and highly effective for detecting, monitoring, and measuring fluorescent agents, since methods such as these can generate either qualitative or quantitative information and detection can be achieved either by direct visual observation or by instrumentation.

For many applications that utilize fluorescent dyes as tracers, it is necessary to chemically react the dye with a biologically active ligand such as a cell, tissue, protein, antibody, enzyme, drug, hormone, nucleotide, nucleic acid, polysaccharide, lipid or other biomolecule to make a fluorescent ligand analog or to react the dye with natural or synthetic polymers. With these synthetic probes, the biomolecule frequently confers a specificity for a biochemical interaction that is under investigation and the fluorescent dye provides the method for detection and/or quantification of the interaction. Thus, useful dyes are based on a versatile fluorescent nucleus that allows the preparation of reactive derivatives of several different types that exhibit reactivity toward a variety of chemically reactive sites.

There is a recognized need for suitable fluorophores, particularly reactive fluorophores, for applications in multicolor, multiplexed applications, such as microscopy, flow cytometry, immunoassays, and nucleic acid sequencing. Most of the dyes proposed for these applications have longer wavelength emission than fluorescein. Since fluorescein has essentially no fluorescence below 490 nm, a well-designed assay system utilizing fluorescein and a second fluorophore that has a strong emission below this wavelength, would be useful for multiplex assays.

A number of dyes have been proposed in the literature that can be excited and detected at wavelengths less than 500 nm. Several chemically reactive fluorophores that can be excited in the near ultraviolet and short wavelength visible region of the spectrum have been described. Exemplary tracers are derived from naphthalene derivatives such as 5-dimethylaminonaphthalene-1-sulfonic acid (Dansyl) (Weber, *Biochem. J.* 41: 145 (1952); Rinderknecht, *Experientin* 16: 430 (1960)) 3-(isothiocyanato)naphthalene-1,5-disulfonic acid (Braunitzer et al., *Hoppe-Seyler's Z. Physiol. Chem.* 352: 1730 (1971)), and N-(4-methylphenyl)-5-isothiocyanato-1,8-naphthalimide (Khalaf & Rimpler, *Hoppe-Seyler's Z Physiol. Chem.* 358: 505 (1977)); pyrene derivatives such as pyrene-1-butyric acid (PBA) (Malencik & Anderson, *Biochemistry* 11: 3022 (1972)), 8-isothiocyanatopyrene-1,3,6-trisulfonic acid (IPTS) (Braunitzer, et al., *Hoppe-Seyler's Z Physiol. Chem.* 354: 1536 (1973)) and 8-hydroxypyrene-1,3,6-trisulfonyl chloride (Wolfbeis, *Fresenies Z. Anal. Chem.* 320: 271 (1985)); stilbene derivatives such as 4-acetamido-4'-isothiocyanatostilbene-2,2'-disulfonic acid (SITS) (Cornelisse & Ploem, *J. Histochem. Cytochem.* 24: 72 (1976)); and coumarin dyes such as 3-carboxy-7-hydroxycoumarin (Baker & Collis, *J. Chem. Soc.* 1949, S 12 (1949)), 7-hydroxy-4-methylumbelliferone-3-acetic acid (4-MUA) (Khalfan, et al., *Biochem. J.* 209: 265 (1983)), 7-amino-4-methylcoumarin-3-acetic acid (AMCA) (Khalfan, et al., *Histochem. J.* 18: 497 (1986)) and 7-diethylaminocoumarin (Staines et al., *J. Histochem. Cytochem.* 36:145 (1988))

The existing, reactive, blue-fluorescent fluorophores generally have a weak absorptivity (extinction coefficients of less than 20,000 cm$^{-1}$ M$^{-1}$ at their absorbance maxima), relatively low quantum yields, and/or or not particularly well solubilized in aqueous environments. Such properties are less than ideal for a fluorophore of interest for biological applications.

For example, the large Stokes' shifts and wide emission band-widths of many art-recognized dyes result in significant residual fluorescence background from the ultraviolet excited dyes at wavelengths typically used for detection of fluorescein emission (typically 515 to 525 nm). With the exception of 4-MUA, the potential alternative dyes are not optimally suited for excitation with the strongest emission lines of the most commonly available sources, such as the 365 nm line of the mercury arc lamp. Moreover, fluorescence of many of the art-recognized dyes is frequently quenched in aqueous solution, resulting in low quantum yields. The lower quantum yield decreases the detection sensitivity or requires use of disproportionately larger quantities of the less fluorescent dye.

Despite their acceptance as fluorescent tracers, coumarin derivatives have deficiencies that preclude or make more difficult some useful applications. The reactive derivatives of aminocoumarins are quite lipophilic and insoluble in aqueous preparations. Additionally, hydroxycoumarin derivatives typically exhibit $pK_a$ values near or above 7.0 and show a pH dependent absorption spectrum that displays a decreased fluorescence in the physiological pH range.

While having other desirable properties of high absorbance and high water solubility, SITS has a very low fluorescence yield in water and is photolytically isomerized to the non-fluorescent cis isomer. Despite the commercial availability of SITS for many years, use of SITS to form fluorescent conjugates has not been widely adopted due to the low fluorescence yield. SITS and related stilbene derivatives also have been found to have an inhibitory effect on anion transport systems in red blood cells (Barzilay, et al., *Membrane Biochemistry* 2: 227 (1979)) and on microsomal glucose-6-phosphatase (Speth & Schulze, *Eur. J. Biochem.* 174: 111 (1988)). Another drawback of SITS is the short wavelength absorption maximum (<350 nm). Ultraviolet excitation of SITS can result in cell injury and death in applications where fluorescence measurements are performed on living cells. Autofluorescence of proteins, nucleic acids and other biomolecules present in cells is also increased with shorter wavelength excitation.

Furthermore, the emission spectra of stilbene, napthalene and coumarin derivatives have a very broad long wavelength component which greatly increases the fluorescence background at wavelengths used for detection of other dyes such as fluorescein, Lucifer Yellow and tetramethylrhodamine in applications such as DNA sequencing, developmental tracers and flow cytometry that require detection of multiple dyes and dye conjugates.

With the exception of SITS and the isothiocyanate of pyrenetrisulfonic acid, the solubility in aqueous solution of the commonly used reactive forms of these dyes is very low, necessitating use of organic solvent co-mixtures in forming dye conjugates with most biopolymers. Reactive dye derivatives such as succinimidyl pyrene-1-butyrate and the succinimidyl ester of AMCA are quite lipophilic and insoluble in the aqueous solutions required for fluorescent labelling of proteins, polysaccharides and other biomolecules.

In certain applications, it is desired to utilize a rigid fluorophore to assess the local environment proximate the fluorophore. If the motional correlation times of the fluorophore are long relative to its fluorescence lifetime, the environment in which the fluorophore is located can be probed by a variety of energy transfer experiments, including fluorescence resonance energy transfer, a method that can be used to determine the distance between an immobilized fluorophore and a resonant group such as tryptophan. A rigid fluorophore will generally exhibit motional correlation times that are enhanced relative to more flexible or sterically undemanding fluorophores, thereby enhancing the energy transfer between the fluorophore and another group.

Haugland et al. disclosed reactive tri-sulfonic acid pyrene fluorophores, however, the linker arms incorporated into these agents do not incorporate identical rigid structures, nor do they include the rigid groups as near to the fluorophore, as the compounds of the invention (U.S. Pat. No. 5,132,432). For example, Haugland et al. discloses compounds that include a ring structure formed with nitrogen atom (NRR') in the —OCH$_2$CO$_2$N(CH$_2$)$_v$NRR', in which v is 2 or 5. In contrast, exemplary compounds of the invention include a cyclic structure formed between the nitrogen and R' and R" moieties of a linker arm of formula —OCH$_2$CO$_2$NR'R".

In view of the above, a fluorophore having a reactive group attached to the fluorescent nucleus of the fluorophore via a rigid linker arm, which is also water soluble, and highly fluorescent within a narrow wavelength range would be a highly desirable addition to the art-recognized array of reactive fluorophores. The present invention provides such fluorescent agents, conjugates incorporating the agents and methods of using the agents and their conjugates.

BRIEF SUMMARY OF THE INVENTION

The invention provides a novel class of reactive fluorescent pyrene sulfonic acid agents. Exemplary agents of the invention have high absorptivity (extinction coefficients of greater than 25,000 cm$^{-1}$ M$^{-1}$) and high quantum yields. The agents are highly fluorescent, soluble in water and have uniquely low background fluorescence at the emission of a number of commonly used fluorophores, e.g., fluorescein, rendering the agents and their conjugates highly useful for multi-color, or multiplexing assays.

The dyes of the present invention are useful for multicolor applications ("multiplexing"). The dyes have a high fluorescence quantum yield with a narrow emission peak at a wavelength that can be sufficiently differentiated from other dyes commonly used in fluorescent assays. Thus, the emission of the dyes of exemplary compounds of the invention have little or no spectral overlap with the emission band of the other fluorophores, e.g., fluorescein.

Moreover, the dyes of the invention have a high absorptivity as measured by extinction coefficient. The dyes of the present invention can be excited with the most intense emission lines of the common excitation sources such as the 365 nm line of the mercury arc lamp. Excitation below 365 nm is undesirable since it can result in cell injury or death in applications where fluorescence measurements are performed on living cells. Furthermore, autofluorescence of proteins, nucleic acids and other biomolecules present in cells (especially NADH which has peak absorbance at 340 nm and peak emission at 460 nm) is also increased with shorter wavelength excitation. Use of wavelengths longer than 350 nm also permits use of less expensive glass optics instead of quartz optics.

The invention also provides dyes (and their reactive analogues) that are highly water soluble, thus of particular use in aqueous environments, such as those used for modification of cells and biopolymers. Furthermore, the dyes of the invention display high stability towards the excitation light (i.e., resistance to photobleaching), enhancing the utility of the dye for quantitative measurements and permitting extended illumination time and higher lamp intensities for increased sensitivity.

Moreover, for quantitative measurements, the present dyes generally have emission intensities that are relatively insensitive to properties of the solution. The measured signal from such dyes is generally proportional only to the absolute quantity of dye present and is independent of environmental effects such as pH, viscosity and polarity.

Additionally, the dyes of the present invention have an intrinsically low biological activity and/or toxicity The compounds of the invention preferably include a rigid linker arm interposed between the reactive group (or bond to a component of a conjugate) and the fluorescent nucleus. Thus, the compounds of the invention are also useful for assays in which fluorophores conjugated to a selected site, exhibiting minimal motional freedom within that site. Exemplary assays in which the probes of the invention find use include the determination of the structure of enzyme active sites, studies of membrane dynamics and investigations of ligand-receptor interactions. Other applications in which a rigid, reactive fluorophore having the desirable properties set forth above are of use will be apparent to those of skill in the art.

Thus, in a first aspect, the present invention provides an agent in which a pyrene moiety having at least one sulfonic acid moiety (either ionized or protonated) is functionalized with a linker arm that bears a reactive group, or is conjugated to a component of a conjugate. The linker arm has the formula:

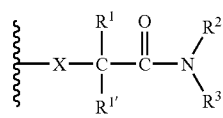

in which the symbol X represents NH, O or S. $R^1$ and $R^{1'}$ are independently selected from H, substituted or unsubstituted alkyl and substituted or unsubstituted heteroalkyl. The symbol $X^1$ represents O, S or NH. The moieties corresponding to $R^2$ and $R^3$ are independently selected from substituted or unsubstituted alkyl and substituted or unsubstituted heteroalkyl. At least one of $R^2$ and $R^3$ preferably includes a reactive functional group. In an exemplary embodiment, $R^2$ and $R^3$ together with the nitrogen to which they are bound are joined in a ring, such as a 4-6-membered heterocyclic ring that optionally includes heteroatoms other than the nitrogen to which $R^2$ and $R^3$ are bound.

The pyrene moiety of the agents can be further substituted with one or more "aryl group substituents" as defined herein, such as OH, sulfo, nitro, carboxyl, carboxylate esters, halogen, substituted or unsubstituted alkyl, substituted or unsubstituted heteroalkyl (e.g., alkoxy, alkylthio, aminoalkyl, etc.), substituted or unsubstituted aryl, substituted or unsubstituted heteroaryl, substituted or unsubstituted heterocycloalkyl and a reactive group.

The invention also provides conjugates of the reactive agents described above.

In still a further aspect, the invention provides kits that include a compound of the invention and directions for making use of the compound.

Other aspects, objects and advantages of the present invention will be apparent from the detailed description that follows.

DETAILED DESCRIPTION OF THE INVENTION

Introduction

Figure 1A:
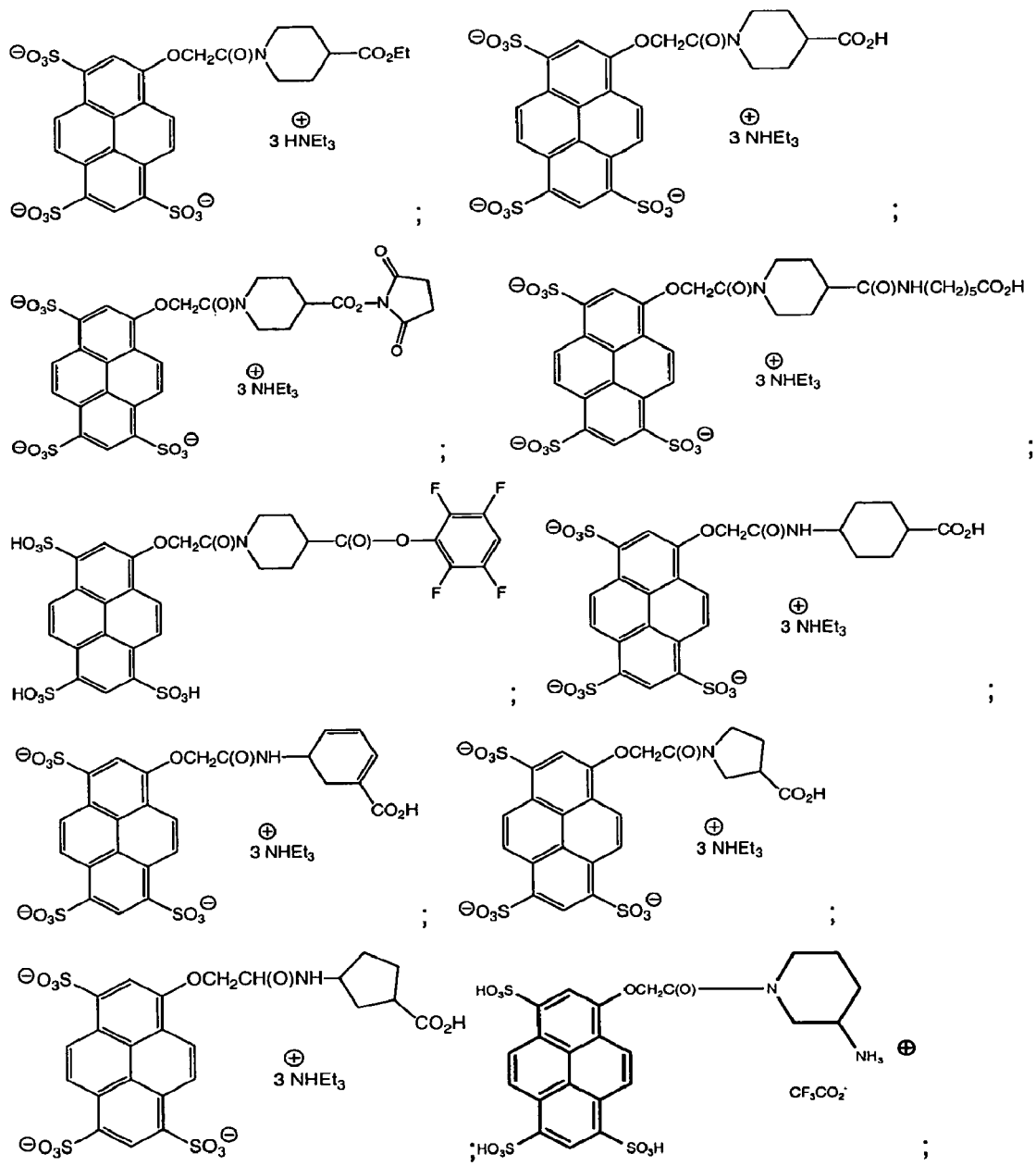
FIG. 1 displays exemplary compounds of the invention.
Figure 1B:
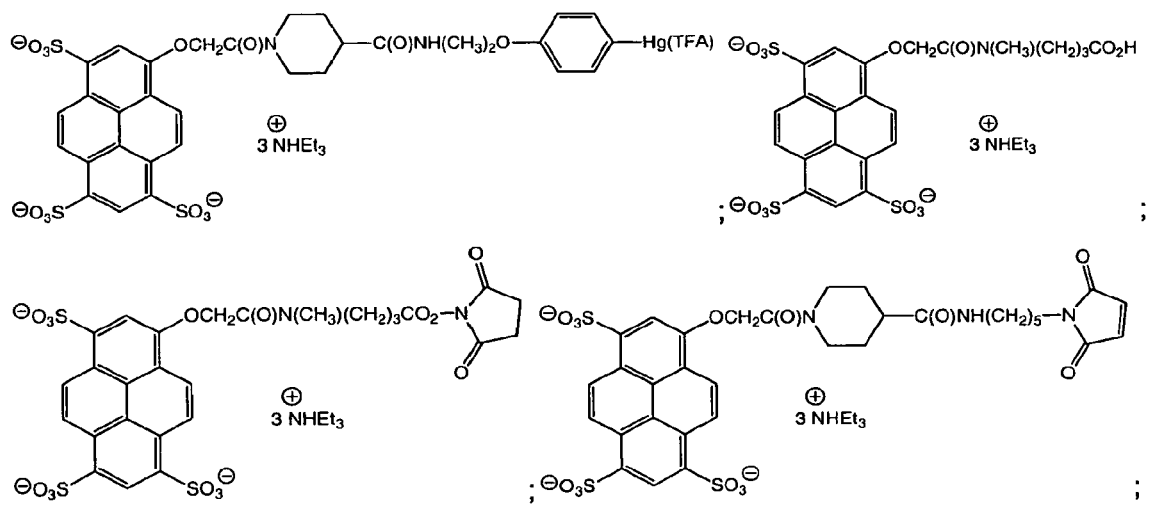

There is a continuous and expanding need for rapid, highly specific methods of detecting and quantifying chemical, biochemical and biological analytes in research and diagnostic mixtures. Of particular value are methods for measuring small quantities of nucleic acids, peptides (e.g., enzymes), pharmaceuticals, metabolites, microorganisms and other materials of diagnostic value. Examples of such materials include narcotics and poisons, drugs administered for therapeutic purposes, hormones, pathogenic microorganisms and viruses, antibodies, and enzymes and nucleic acids, particularly those implicated in disease states.

One method of detecting an analyte relies on directly or indirectly labeling the analyte or other component of the analysis mixture with a fluorescent species. Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling.

As discussed herein, the present invention provides a new class of fluorescent probes that are of use in a variety of analytical techniques.

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a fusion protein" includes a plurality of proteins and reference to "a fluorescent compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The symbol ⁓, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or —N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution," as used herein, refers to a solution that is predominantly water and retains the solution characteristics of water. Where the aqueous solution contains solvents in addition to water, water is typically the predominant solvent.

The term "attachment site" as used herein refers to a site on a moiety or a molecule, e.g. a biomolecule, quencher, a fluorescent dye, an avidin, or an antibody, which is covalently attached to, or capable of being covalently attached to a linker, a compound of the invention or another moiety.

The term "detectable response," as used herein, refers to a change in or the occurrence of, a signal that is directly or indirectly detectable either by observation or by instrumentation. Exemplary detectable responses include an optical response resulting in a change in the wavelength distribution patterns or intensity of absorbance or fluorescence or a change in light scatter, fluorescence lifetime, fluorescence polarization, or a combination of the above parameters.

The term "enzyme," as used herein, refers to a peptide with catalytic activity.

The term "fluorescent labeled component," as used herein, refers to a compound of the present invention that is covalently bonded to a biological or a non-biological component. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "Linker" or "L", as used herein, refers to a single covalent bond or a series of stable covalent bonds incorporating 1-20 nonhydrogen atoms selected from the group consisting of C, N, O, S and P that covalently attach the fluorescent compounds to another moiety such as a chemically reactive group or a conjugated substance including biological and non-biological substances. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and hetero-bifunctional) spacer arms are commercially available.

An exemplary cleavable group, an ester, can be cleaved by a reagent, e.g. sodium hydroxide, resulting in a carboxylate- and hydroxyl-containing fragments.

The linker can be used to attach a reactive fluorescent agent of the invention to another component of a conjugate, such as a targeting moiety (e.g., antibody, ligand, non-covalent protein-binding group, etc.), an analyte, a biomolecule, a drug and the like.

"Non-covalent protein binding groups" are moieties that interact with an intact or denatured polypeptide in an associative manner. The interaction may be either reversible or irreversible in a biological milieu. The incorporation of a "non-covalent protein binding group" into a fluorescent compound of the invention provides the compound with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a quencher, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Protecting group," as used herein, refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage resulting in a fluorescent labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "sample" as used herein refers to any material that may contain a analyte for detection or quantification. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like.

Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "salt thereof," includes salts of the agents of the invention and their conjugates, which are preferably prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The term "targeting group" refers to a moiety that is: (1) able to actively direct the entity to which it is attached (e.g., a fluorescent moiety) to a target region, e.g., a cell; or (2) is preferentially passively absorbed by or entrained within a target region. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly (ethers), dendrimers, poly(amino acids) and so forth.

The Compounds

In a first aspect, the present invention provides a reactive fluorescent agent in which a pyrene moiety having at least one sulfonic acid moiety (either ionized or protonated) is functionalized with a linker arm that bears a reactive group, or is conjugated to a component of a conjugate. Thus, the following discussion is relevant both to the reactive fluorophore-linker constructs of the invention and conjugates that incorporate the linker arm functionalized-pyrene species disclosed herein.

In a first aspect, the linker arm has a structure according to Formula (I):

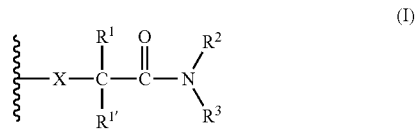

in which the symbol X represents NH, O or S. $R^1$ and $R^{1'}$ are independently selected from H, substituted or unsubstituted alkyl and substituted or unsubstituted heteroalkyl. Both $R^2$ and $R^3$ are not H. The symbol $X^1$ represents O, S or NH. The moieties corresponding to $R^2$ and $R^3$ are independently selected from substituted or unsubstituted alkyl and substituted or unsubstituted heteroalkyl. At least one of $R^2$ and $R^3$ preferably includes a reactive functional group or a bond to a component of a conjugate. In an exemplary embodiment, $R^2$ and $R^3$ together with the nitrogen to which they are bound are joined in a ring, such as a 4-6-membered heterocyclic ring that optionally includes heteroatoms other than the nitrogen to which $R^2$ and $R^3$ are bound. When $R^2$ and $R^3$ are joined in a ring, the ring preferably includes at least one reactive group as a substituent. Alternatively, the ring structure includes a bond to a component of a conjugate.

In an exemplary embodiment, $R^2$ and $R^3$ are both linear moieties selected from substituted or unsubstituted alkyl or substituted or unsubstituted heteroalkyl and at least one of $R^3$ and $R^4$ includes a reactive group or a bond to a component of a conjugate. The structure and preparation of an exemplary compound of this motif, in which $R^2$ is methyl and $R^3$ is an alkyl group substituted with a carboxyl moiety (or its active ester), are set forth in Examples 12 and 13.

In those compounds of the invention in which $R^2$ is H, $R^3$ is preferably a cyclic structure substituted with a reactive group, a moiety comprising a reactive group or a component of a conjugate.

In another exemplary embodiment, $R^2$, $R^3$ and the nitrogen to which they are attached are joined, forming a cyclic structure according to Formula II:

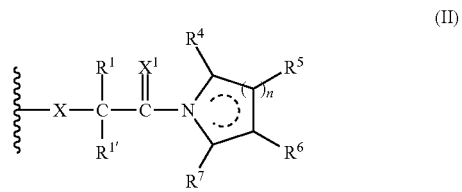

in which $R^1$, $R^{1'}$, $R^2$, X, and $X^1$ are as described previously. $R^4$, $R^5$, $R^6$ and $R^7$ are generally "alkyl group substituents" or "aryl group substituents," as defined herein; preferably at least one of these substituents is a reactive group (or a bond to a component of a conjugate) or is a moiety that comprises a reactive group (or a bond to a component of a conjugate). The index "n" represents the integer 1 or 2. When "n" is 2, each $R^5$ moiety is independently selected. The dashed line within the ring structure indicates that the ring optionally includes one or more double bonds. The ring structure in Formula II encompasses both aromatic and non-aromatic heterocycles.

Exemplary unsaturated ring systems include at least one degree of unsaturation and are optionally are able to participate in Diels-Alder cyclizations and Michael additions. Such ring systems include, but are not limited to:

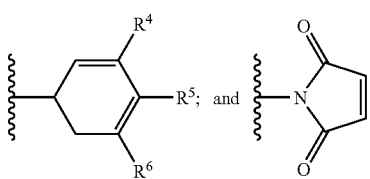

in which the point of attachment shown in the six-member ring is the amide nitrogen; similarly, the endocyclic nitrogen of the five-member ring is the amide nitrogen of Formula II.

In a further exemplary embodiment, the invention provides reactive fluorophores and conjugates thereof in which the cyclic ring system is saturated:

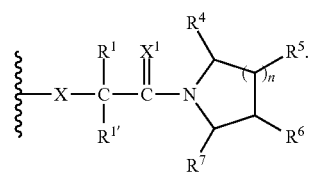
(III)

Certain of the compounds according to Formula III include a six-member ring system:

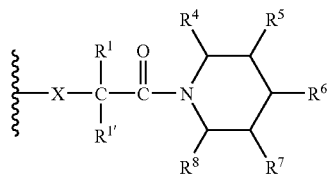
(IV)

in which $R^8$ is independently selected from the groups set forth above in the context of $R^4$-$R^7$.

Selected compounds of the invention include ring systems pendent from the amide nitrogen, rather than endocyclically encompassing this atom:

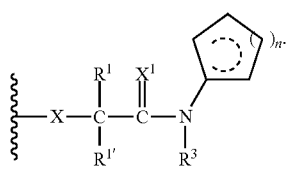
(V)

In each of Formulae III-V, above, the substituents, variable atoms and indexes are the same as those discussed in the context of Formula II.

As discussed above, the compounds of the invention include a fluorescent moiety that is based upon a pyrene nucleus substituted with at least one sulfonic acid moiety or a salt thereof. An exemplary pyrene nucleus of use in the present invention has a structure according to Formula VI:

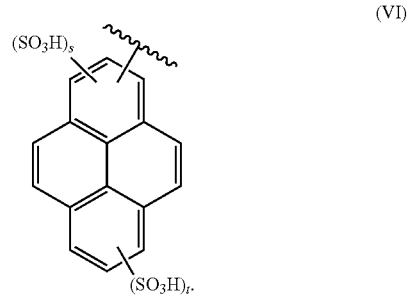
(VI)

The indexes "s" and "t" independently represent the integers 0, 1, 2 and 3, with the proviso that at least one of "s" and "t" is 1. The atom pendent from the point of attachment shown in Formula VI is the ether X moiety, e.g., and ether oxygen, of the linker shown in Formula I.

Although the linker is shown as being appended to the "topmost" six-member ring of the pyrene nucleus, those of skill will understand that the present invention is not limited to such structures; the linker can be attached to any other ring of the pyrene nucleus.

An exemplary pyrene nucleus useful in the compounds of the invention has the formula:

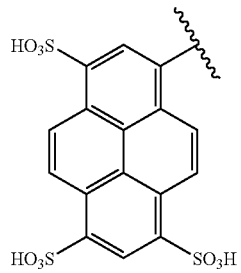
(VII)

The pyrene moiety of the agents can be further substituted with one or more "aryl group substituents" as defined herein, such as OH, sulfo, nitro, carboxyl, carboxylate esters, halogen, substituted or unsubstituted alkyl, substituted or unsubstituted heteroalkyl (e.g., alkoxy, alkylthio, aminoalkyl, etc.), substituted or unsubstituted aryl, substituted or unsubstituted heteroaryl, substituted or unsubstituted heterocycloalkyl and a reactive group.

Synthesis

In an exemplary route the compounds of the invention are prepared starting with a pyrenyloxyacetic acid bearing at least three sulfonic acid moieties. As shown in Scheme 1, the oxyacetic acid moiety is converted to the corresponding amide by activating the carboxylic acid moiety and reacting it with an amine.

Scheme 1

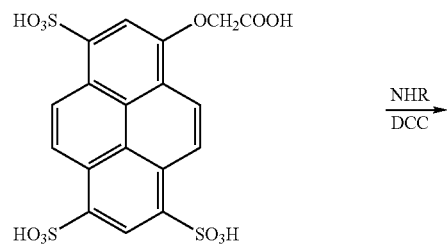

-continued

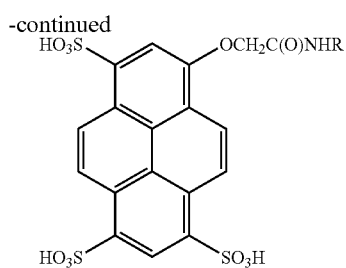

Once the amine carboxylic acid is converted to the amide, the substituent on the amine or on the pyrene are readily manipulated.

As set forth in Scheme 2, an exemplary amine is ethyl isonipecotate:

Scheme 2

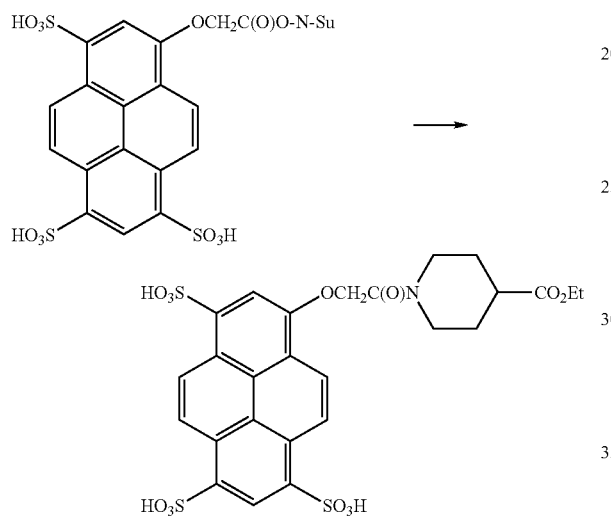

As set forth in Scheme 3, an exemplary reactive group, a carboxylic acid formed by hydrolysis of the corresponding ester, is readily activated and converted into a desired group.

In Scheme 3, the carboxylic ester moiety of the cyclohexyl amide is hydrolyzed by the action of LiOH. The resulting carboxylic acid can be activated in situ by various agents, e.g., dicyclohexylcarbodiimide. In a complementary manner, the carboxylic acid is also readily converted to reactive derivatives, such as active esters.

In another exemplary embodiment, the amide nitrogen is exo- rather than endo-cyclic to the ring system. Such compounds the of invention are readily prepared by routes such as that set forth in Scheme 4:

Scheme 4

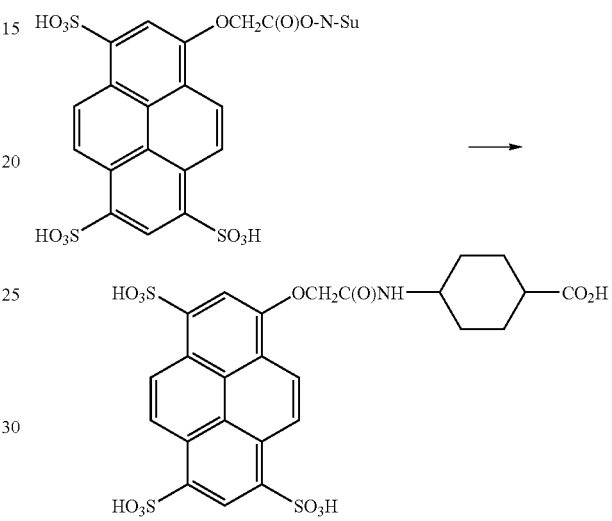

in which the N-hydroxysuccinimide active ester is reacted with cis-4-amino-1-cyclohexanecarboxylic acid, affording the corresponding amide.

Non-cyclic amines are incorporated into the compounds of the invention by methods analogous to those set forth above.

Several other moieties are optionally present during these synthetic steps; they may either be protected with a protecting Scheme 3

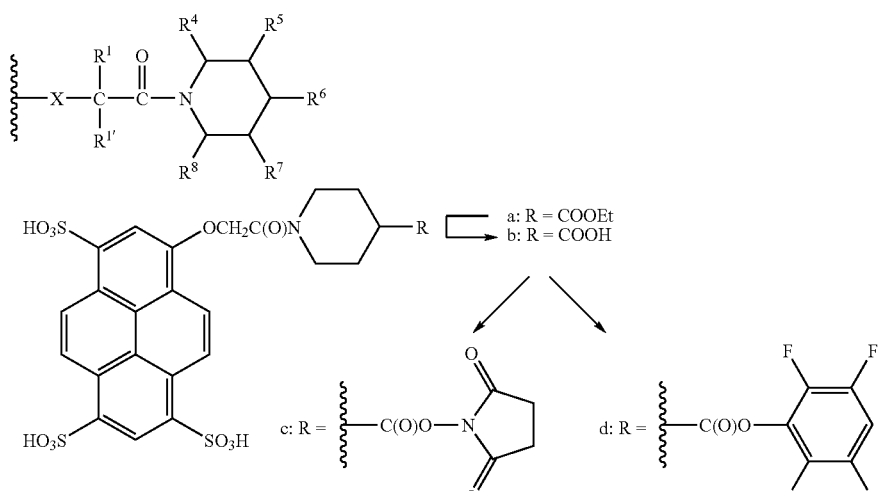

a. LiOH; b. N-hyroxysuccinimide/DSC/DMAP; c. N-hydroxysuccinimide; d. 2, 3, 5, 6-tetrafluorophenyl trifluoroacetate/Et₃N.

group or resistant to the steps required for synthesis of the compound. Exemplary moieties include alkyl, carboxy, amino, acyl, nitro, cyano, carboxyalkyl, chloro, bromo, iodo, alkoxy and hydroxy. Hydroxy moieties may also be formed during cleavage of alkoxy groups present in the starting material.

Reactive Groups

Selected compounds of the invention include one or more reactive group within their structure. The reactive group provides a locus for attaching a compound according to Formulae I-VIII to another species, generally referred to herein as a "component" of a conjugate. Exemplary components include biological or non-biological molecules, linkers, solid supports, targeting agents and the like. The reactive group reacts with a functional group of complementary reactivity at the "attachment site" of the component of the conjugate. The reaction leads to the formation of a covalent linkage between the compound of the invention and the component of the conjugate.

Reactive groups or reactive group precursors are positioned during the formation of the present compounds. Thus, compounds incorporating a reactive group can be reacted with and attached to a wide variety of biomolecules or non-biomolecules that contain or are modified to contain functional groups with suitable reactivity. When a labeled component includes a fluorescent compound of the invention, then this conjugate typically is imbued with the fluorescent properties of the compounds of the invention. The present fluorescent compounds can also function as reporter molecules for a labeled components in which the fluorescent properties of the compound are not employed, e.g., the compound is used as a quencher, hapten, etc.

The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive group and the component to be conjugated results in one or more atoms of the reactive group to be incorporated into a new linkage attaching the compound or reagents of the invention to the biological or non-biological component. Selected examples of functional groups and linkages are shown in Table 1, where the reaction of an electrophilic group and a nucleophilic group yields a covalent linkage.

TABLE 1

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |

TABLE 1-continued

Examples of some routes to useful covalent linkages with electrophile and nucleophile reactive groups

| Electrophilic Group | Nucleophilic Group | Resulting Covalent Linkage |
|---|---|---|
| anhydrides | amines/anilines | carboxamides |
| aryl halides | thiols | thiophenols |
| aryl halides | mines | ryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a leaving group (e.g. oxysuccinimidyl (—OC$_4$H$_4$O$_2$) oxysulfosuccinimidyl (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof,used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$alkoxy; or cyclohexyl, 3-dimethylaminopropyl, or N-morpholinoethyl).
**Acyl azides can also rearrange to isocyanates Preferred reactive groups incorporated into the compounds of the invention react with an amine, a thiol or an alcohol. In one embodiment, the reactive group is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine, an imido ester, an isocyanate, an isothiocyanate, a maleimide, a phosphoramidite, a sulfonyl halide, or a thiol group.

Where the reactive group is an activated ester of a carboxylic acid, the resulting compound is particularly useful for preparing conjugates of proteins, nucleic acids, e.g., nucleotides and oligonucleotides, or haptens. Where the reactive group is a maleimide or haloacetamide the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation or forms the substrate of a microarray or biochip.

Preferably, the reactive group is a succinimidyl ester of a carboxylic acid, a haloacetamide, a hydrazine, an isothiocyanate, a maleimide group, an aliphatic amine, a silyl halide, or a psoralen. More preferably, the reactive group is a succinimidyl ester of a carboxylic acid, a maleimide, an iodoacetamide, or a silyl halide.

In an exemplary embodiment, the compounds of the present invention that include a reactive group further comprise a linker. The linker serves to covalently attach the reactive group to the compound. When present, the linker is a single covalent bond or a branched- or straight-chain, saturated or unsaturated chain of atoms. Examples of L include substituted or unsubstituted polyalkylene, arylene, alkylarylene, arylenealkyl, or arylthio.

Thus, the reactive group may be directly attached (where Linker is a single bond) to the present compounds or attached through a series of stable bonds. When the linker is a series of stable covalent bonds the linker typically incorporates 1-20, more preferably 1-15, non-hydrogen atoms selected from the group consisting of C, N, O, S and P. In addition, the covalent linkage can incorporate a platinum atom, such as described in U.S. Pat. No. 5,714,327.

The linker may be any combination of chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Exemplary components of the linker include ether, thioether, thiourea, amine, ester, carboxamide, sulfonamide, hydrazide bonds and aromatic or heteroaromatic bonds.

An exemplary linker is a combination of single carbon-carbon bonds and carboxamide, sulfonamide or thioether bonds. The bonds of the linker typically result in the following moieties being in the linker: ether, thioether, carboxamide, thiourea, sulfonamide, urea, urethane, hydrazine, alkyl, aryl, heteroaryl, alkoxy, cycloalkyl and amine moieties.

Any combination of linkers may be present in the reactive compounds of the invention. An exemplary compound of the present invention, when attached to more than one reactive group will have one or two linkers attached that may be the same or different. The linker may also be substituted to alter a physical property of the present compounds, such as hydrophilicity, solubility and spectral properties of the compound.

The selection of a covalent linkage to attach the dye to the labeled component typically depends on the chemically reactive group on the component to be conjugated. The discussion regarding reactive groups in the section immediately preceding is relevant here as well. Exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A labeled component may be conjugated to more than one dye, which may be the same or different, or to a substance that is additionally modified by a hapten. Although some selectivity can be obtained by careful control of the reaction conditions, selectivity of labeling is best obtained by selection of an appropriate reactive compound.

Conjugates

In another aspect, the invention provides a conjugate formed between a reactive agent of the invention and another species, referred to herein as "a component." The conjugate includes a bond that is formed by reaction of the reactive group of the agent with a reactive moiety on the component. In an exemplary embodiment, at least one of $R^2$ and $R^3$ includes the bond to the component.

A variety of labeled conjugates may be prepared using the reactive compounds of the invention, including present labeled components of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is an amino acid, peptide, protein, polysaccharide, nucleotide, nucleoside, oligonucleotide, nucleic acid, hapten, a psoralen, drug, a hormone, lipid, phospholipid, lipoprotein, lipopolysaccharide, liposome, lipophilic polymer, a synthetic polymer, polymeric microparticle, biological cell, a virus and combinations thereof. In one embodiment of the invention, the component is labeled with a plurality of compounds of the present invention, which may be the same or different.

In one embodiment, the labeled component comprises an amino acid (including those that are protected or are substituted by phosphates, carbohydrates, or $C_1$ to $C_{22}$ carboxylic acids), or a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Also preferred are peptides that serve as organelle localization peptides, that is, peptides that serve to target the conjugated compound for localization within a particular cellular substructure by cellular transport mechanisms. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, or a growth factor. Preferred haptens include biotin, digoxigenin and fluorophores.

In another embodiment, the labeled component comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. Preferably, the conjugated nucleotide is a nucleoside or a deoxynucleoside or a dideoxynucleoside.

Preferred nucleic acid polymer conjugates are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides. The present compounds are optionally attached via one or more purine or pyrimidine bases through an amide, ester, ether or thioether bond; or is attached to the phosphate or carbohydrate by a bond that is an ester, thioester, amide, ether or thioether. Alternatively, the compound is attached by formation of a non-covalent association of the nucleic acid and a photoreactive compound of the invention, followed by illumination, resulting in covalently bound compound. Nucleotide conjugates of the invention can be incorporated by some DNA polymerases and can be used for in situ hybridization and nucleic acid sequencing (e.g., U.S. Pat. Nos. 5,332,666; 5,171,534; and 4,997,928, all incorporated by reference; and WO Appl. 94/05688).

In another embodiment, the labeled component comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). Preferred polysaccharide conjugates are dextran or FICOLL conjugates.

In another embodiment, the labeled component comprises a lipid (typically having 6-25 carbons), including glycolipids, phospholipids, and sphingolipids. Alternatively, the labeled component comprises a lipid vesicle, such as a liposome, or is a lipoprotein. Some lipophilic substituents are useful for facilitating transport of the conjugated dye into cells or cellular organelles.

In another embodiment, the labeled component includes polymers, polymeric particles, polymeric microparticles including magnetic and non-magnetic microspheres, polymeric membranes, conducting and non-conducting metals and non-metals, and glass and plastic surfaces and particles. Conjugates are typically prepared by chemical modification of a polymer that contains functional groups with suitable chemical reactivity. The conjugated polymer may be organic or inorganic, natural or synthetic. In a preferred embodiment, the present compounds are conjugated to a polymer matrix, such as a polymeric particle or membrane, including membranes suitable for blot assays for nucleic acids or proteins. In another embodiment, the labeled component comprises a glass or silica, which may be formed into an optical fiber or other structure. In another embodiment, the labeled component comprises a poly(ethylene glycol), a poly(acrylate) or a poly(acrylamide).

The conjugated substance is optionally an ion-complexing moiety. While any chelator that binds an ion of interest and gives a change in its fluorescence properties is a suitable conjugate, preferred ion-complexing moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.*, 256: C540 (1989); and pyridyl-based and phenanthroline metal ion chelators, as described in U.S. Pat. No. 5,648,270 to Kuhn et al. (1997).

Fluorescent conjugates of ion-complexing moieties possess utility as indicators for the presence of a desired metal ion. While fluorescent ion-indicators are known in the art, the incorporation of the fluorescent compounds of the present invention imparts the highly advantageous properties of the instant fluorophores onto the resulting ion indicator.

The ion-sensing conjugates of the invention are optionally prepared in chemically reactive forms and further conjugated to polymers such as dextrans to improve their utility as sensors as described in U.S. Pat. Nos. 5,405,975 and 5,453,517.

Alternatively, the conjugates of the present invention are conjugates of cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another exemplary embodiment, the conjugates of the present invention are optionally dye-conjugates of polymers, polymeric particles, polymeric microparticles including magnetic and non-magnetic microspheres, polymeric membranes, conducting and non-conducting metals and non-metals, and glass and plastic surfaces and particles. Conjugates are optionally prepared by copolymerization of a dye that contains an appropriate functionality while preparing the polymer, or by chemical modification of a polymer that contains functional groups with suitable chemical reactivity. In another embodiment of the invention, the conjugated substance is a glass or silica, which may be formed into an optical fiber or other structure.

In an exemplary embodiment, the labeled component comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair and not a compound used to determine the presence of peroxide in a sample. Exemplary binding pairs are set forth in Table 2.

TABLE 2

Representative Specific Binding Pairs

| antigen | antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization Preparation of Conjugates Conjugates of components, e.g., drugs, peptides, toxins, nucleotides, phospholipids and other organic molecules are prepared by organic synthesis methods using the reactive dyes of the invention, are generally prepared by means well recognized in the art (Haugland, MOLECULAR PROBES HANDBOOK, supra, Sets 1-7, (1992)). Preferably, conjugation to form a covalent bond consists of simply mixing the reactive dyes of the present invention in a suitable solvent in which both the reactive dye and the substance to be conjugated are soluble. The reaction preferably proceeds spontaneously without added reagents at room temperature or below. For those reactive dyes that are photoactivated, conjugation is facilitated by illumination of the reaction mixture to activate the reactive dye. Chemical modification of water-insoluble substances, so that a desired dye-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive dyes to make them more readily soluble in organic solvents. Many of the dyes of the present invention are readily dissolved in aqueous solution by adjusting the pH of the solution to about 6 or higher.

Preparation of peptide or protein conjugates typically comprises first dissolving the protein to be conjugated in aqueous buffer at about 1-10 mg/mL at room temperature or below.

Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive dye is then dissolved in a nonhydroxylic solvent (usually DMSO or DMF) in an amount sufficient to give a suitable degree of conjugation when added to a solution of the protein to be conjugated. The appropriate amount of dye for any protein or other component is conveniently predetermined by experimentation in which variable amounts of the dye are added to the protein, the conjugate is chromatographically purified to separate unconjugated dye and the dye-protein conjugate is tested in its desired application.

Following addition of the reactive dye to the component solution, the mixture is incubated for a suitable period (typically about 1 hour at room temperature to several hours on ice), the excess dye is removed by gel filtration, dialysis, HPLC, adsorption on an ion exchange or hydrophobic polymer or other suitable means. The dye-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of dye substitution is determined from the long wavelength absorption of the dye-protein conjugate by using the extinction coefficient of the unreacted dye at its long wavelength absorption peak, the unmodified protein's absorption peak in the ultraviolet and by correcting the UV absorption of the conjugate for absorption by the dye in the UV.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the dyes, an excess of dye is typically used, relative to the expected degree of dye substitution. Any residual, unreacted dye or a dye hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the fluorophore, fluorogen or the conjugated substance through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Methods

The present invention also provides methods of using the compounds described herein to detect an analyte in a sample. Those of skill in the art will appreciate that this focus is for clarity of illustration and does not limit the scope of the methods in which the compounds of the invention find use.

In other embodiments, the compounds of the present invention are utilized to stain a sample to give a detectable optical response under desired conditions by a) preparing a dye solution comprising a dye compound described above, at a concentration sufficient to yield a detectable optical response under the desired conditions; combining the sample of interest with the dye solution for a period of time sufficient for the dye compound to yield a detectable optical response under the desired conditions; and c) illuminating the sample at a wavelength selected to elicit the optical response. Optionally, the sample is washed to remove residual, excess or unbound dye. The dye compound typically forms a covalent or noncovalent association or complex with an element of the sample, or is simply present within the bounds of the sample or portion of the sample.

In one embodiment, the staining is used to determine a specified characteristic of the sample by further comparing the optical response with a standard or expected response. For example, the dye solution is used to monitor specific components of the sample with respect to their spatial and temporal distribution in the sample. Alternatively, the dye preferentially binds to a specific analyte in a sample, enabling the researcher to determine the presence or quantity of that specific analyte. In another embodiment, the dye is used to analyze the sample for the presence of a mechanism that responds specifically to the dye compound, such as oxidation or reduction. The desired analysis to be performed determines the composition of the dye solution and chemical nature of the dye itself. In another example, the dye is bound by an antibody directed against the dye itself, typically resulting in the fluorescence quenching of the dye.

For biological applications, the dye solution is typically an aqueous or mostly aqueous solution that comprises one or more of the described dye compounds. In one aspect of the invention, the dye solution comprises a fluorophore as described above; alternatively, the dye solution comprises a dye compound that is a reactive dye analog, as previously described.

In yet another exemplary embodiment, the dye solution includes a dye conjugate as described above.

a composition that includes a first conjugate of the invention in combination with a second conjugate. The second conjugate includes a component that is covalently bonded to a second fluorophore. The first and second fluorophore have different structures and preferably fluoresce at different wavelengths. Even more preferably, the first and second fluorophores are selected so that their fluorescence emissions essentially do not overlap.

The fluorophore on the second conjugate can include substantially any fluorescent structure known in the art including, but not limited to, small organic fluorophores, fluorescent proteins, and reporter groups that are not necessarily fluorescent but which, under correct conditions, convert a fluorogenic substrate into a fluorophore, e.g., horseradish peroxidase. Exemplary second fluorophores of use in the present invention include those that include a moiety that is a member selected from a coumarin, a xanthene (e.g., fluorescein), a cyanine, a pyrene, a borapolyazaindacene, an oxazine, and bimane.

The components of the mixture of the invention may be the same or a different molecule. The discussion herein pertaining to the identity of various components is generally applicable to this embodiment of the invention.

In another exemplary embodiment, at least one of the first and second conjugates is bound to a molecule for which it is a binding partner.

The present invention also provides a method for detecting an analyte in a sample. The method includes contacting the sample with a conjugate of the invention in which the component is a binding partner for the analyte. The mixture of the conjugate and the analyte is incubated under any appropriate conditions for a length of time sufficient for at least a fraction of the analyte population to interact with the conjugate. The interaction can be by any known interaction mechanism, and the present invention is not limited to application with any single type of analyte-conjugate interaction mechanism. The interaction between the analyte and the conjugate results in the formation of a fluorescent analyte. The fluorescent analyte is readily detected and/or quantitated by irradiating it with light of a wavelength that causes the fluorescent analyte to emit fluorescence.

In the method described above, any number or combination of purification, separation or derivatization steps are optionally included as steps in the method. In an exemplary embodiment, the fluorescent analyte is separated from the remainder of the sample, from non-fluorescent analyte or from excess unbound conjugate prior to determining the fluorescence of the fluorescent analyte.

In another exemplary embodiment, the invention provides a multicolor method for detecting an analyte or more than one analyte. For example, when it is desired to detect, and particularly to confirm the identity of an analyte, more than one fluorescent conjugate, preferably fluorescing at different wavelengths can be co-localized on the single analyte The use of more than one color of fluorescent conjugate per analyte provides assays in which specificity is dramatically increased, by requiring that the different colors or color combinations of the fluorescent conjugates coincide spatially during detection. This can dramatically reduce or even eliminate the detection of nonspecifically bound targets or labels, enhancing specificity and sensitivity of the assay. Underlying the improvement represented by the use of multiple differently colored fluorescent conjugates is the improbability of accidentally encountering two or more preselected different colors at the same location at the same time. The improbability increases as more fluorescent conjugates of different colors are used. Alternatively, in another exemplary embodiment, the emission from the two or more differently colored fluorescent conjugates combines to form a third color, which is not otherwise present in the assay.

In an exemplary application of the present method, different features of an analyte, e.g., a cell or epitopes of a molecule, are labeled with different colored fluorescent conjugates. The target is detected and its identity is confirmed using the colocalization or "coincidence" of each color on each target. Coincidence staining allows for the detection and differentiation of different organisms or strains of organisms expressing different surface markers. Moreover, coincidence staining provides a method of distinguishing molecules of different structure down to the level of isomeric differences and differences in stereochemistry.

In the detection of pathogenesis, the most direct analyte is the pathogenic organism itself. In this case, assays preferably identify particular features of the organism such as surface proteins. To further aid in characterization, it is preferred to assay for molecular analytes as well. An example of a molecular analyte is an exotoxin such as cholera toxin. Antigen specific binding receptors are generated that recognize different characteristics of an analyte with high specificity. In the case of molecular analytes, receptors recognize different epitopes of a protein or small molecule, while cellular analytes are recognized through different molecules on the cell surface.

Although the fluorescence from each conjugate can be detected simultaneously, in one embodiment, to facilitate coincidence staining, the fluorescence from each analyte is detected independently.

In another exemplary embodiment, colocalization is used to differentiate between the formation of an analyte-conjugate complex and non-specific binding of the analyte to another species within the assay system. The intrinsic sensitivity of an assay often is limited by non-specific binding of the analyte or other assay mixture components to the substrate. Single analyte coincidence staining can be used to differentiate between specific binding of the analyte to the conjugate and non-specific binding of assay mixture components to the conjugate based on the colocalization of fluorescent conjugate colors. Those of skill in the art will appreciate that coincidence staining as described herein is useful to distinguish non-specific binding in both solid-phase (e.g., gene chip) and solution-based assays Coincidence staining can also be used to identify a single analyte. For example, one may wish to confirm the presence of a selected analyte in a mixture of analytes that are structurally similar (e.g. having a common epitope) or that have similar affinity for the component of the conjugate. In such circumstances, it may prove that the detection of a single epitope is not sufficient for conclusive identification of a target. Measuring the level of 2, preferably 3, more preferably 4 and even more preferably 5 or more markers within a single analyte, provides an unambiguous profile specific for the analyte of interest.

In another exemplary embodiment, the present invention provides a method for distinguishing between organisms expressing the same surface markers. Using coincidence staining, it is possible to identify differences in targets based on the ratio of surface marker expression. For example, despite intense efforts, no single binding-receptor has been found for the unambiguous detection of *B. anthracis* spores, due to extensive cross-reactivity with related *B. cereus* and *B. thuringiensis*, which are genetically a single species (Helgason et al., *Appl. Envir. Microbiol.* 66:2627-2630 (2000)). Despite being of the same species, however, the relative amount of various surface proteins is different between the three bacilli. Thus, multi-point detection of a variety of markers at the single cell level will provide the specificity required to detect *B. anthracis.*

Diagnostic tests that detect the presence or absence of a single marker are unable to distinguish among strains that are nearly identical at the genetic level, highlighting the need for new tools to distinguish between closely related organisms. Epidemics caused by emerging variants of known pathogens are a common theme in infectious diseases (Jiang et al., *Appl Environ Microbiol* 66:148-53 (2000)) (Hedelberg et al. *Nature* 406:477-483 (2000)). There is also the problem of deliberate engineering of pathogens, incorporating virulence determinants from other species. An attack by such pathogens would be misdiagnosed due to the presence of markers not normally found in the attacking pathogen. By probing multiple markers within a single organism, using the methods of the invention, such variants are detected and preferably identified.

Detection by eye is also useful in those embodiments of the invention relying on coincidence staining. The human eye is extremely good at distinguishing between subtly different combinations of colors, especially when the colors are chosen correctly. By way of illustration, it is trivial for people to distinguish between the colors red, green and yellow. Yellow, however, is simply the spectral sum of red and green, so if red and green fluorescent conjugates are used for coincidence staining, positive assay signal can easily be identified by the perceived color, yellow. Other color combinations of use in this embodiment of the invention will be readily apparent to those of skill in the art, such as combinations of red, green and blue to form white.

In another exemplary embodiment the invention provides a method for detecting a first analyte and a second analyte in a sample. The method includes incubating the sample with a composition of the invention that includes first and second fluorescent labeled conjugates. The component of the first conjugate is a binding partner for the first analyte and the component of the second conjugate is a binding partner for the second analyte. The incubation continues for a time and under conditions appropriate to induce an interaction between at least a fraction of the population of the first analyte with the first conjugate. During this incubation period, it is generally preferred that a similar interaction occurs between the second analyte and second conjugate, however, it is within the scope of the invention to change the incubation conditions as necessary to drive the formation of a conjugate-analyte complex between the second conjugate and second analyte.

Following the formation of at least the first analyte-conjugate complex, the sample is illuminated with light of a wavelength appropriate to cause the complex to fluoresce, thereby detecting the first analyte. The second analyte is detected in a similar manner and may be detected simultaneously with the first analyte or by the sequential illumination of the sample with wavelengths appropriate to induce the fluorescence of each fluorescent conjugate.

Solutions of the compounds of the invention are prepared according to methods generally known in the art. As with related known fluorophores and fluorogens, the dyes and dye-conjugates are generally soluble in water and aqueous solutions having a pH greater than or equal to about 6. Stock solutions of pure dyes, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. In general, the amount of dye or conjugate in the dye solution is the minimum amount required to yield detectable staining in the sample within a reasonable time, with minimal background fluorescence or undesirable staining. The exact concentration of dye or dye-conjugate to be used is dependent upon the experimental conditions and the desired results, and optimization of experimental conditions is typically required to determine the best concentration of stain to be used in a given application. The concentration of dye present in the dye solution typically ranges from nanomolar to micromolar. The required concentration for the dye solution is determined by systematic variation in dye or dye-conjugate concentration until satisfactory dye staining is accomplished. The starting ranges are readily determined from methods known in the art for use of similar compounds under comparable conditions for the desired optical response.

For those compounds of the present invention that are substituted by lipophilic moieties, the dye is optionally introduced into living cells by passive permeation through the cellular membranes. Less cell-permeant compounds of the invention can be introduced into cells by pressure microinjection methods, scrape loading techniques (short mechanical disruption of the plasma membrane where the plasma membrane is peeled away from the cytoplasm, the dye is perfused through the sample and the plasma membrane is reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the dye, dye-conjugate or blocked dye into the cellular cytoplasm.

In an exemplary embodiment of the invention, the dye solution comprises a dye that non-covalently associates with organic or inorganic materials. Exemplary embodiments of the dyes that possess a lipophilic substituent can be used to stain lipid assemblies such as biological membranes or liposomes by non-covalent incorporation of the dye compound within the membrane, e.g. for use as probes for membrane structure or for incorporation in liposomes, lipoproteins, films, plastics, lipophilic microspheres or similar materials.

The compounds of the invention are useful as coloring agents, tracers for detecting the flow of fluids such as in angiography, and tracing of fluid flow through gap junctions of neurons according to procedures known in the art for other dyes. The dyes of the invention are also useful in assays as haptens, according to known methods, wherein the dye is recognized by an anti-dye antibody.

The reactive dye compounds of the invention can be used to label cell surfaces, cell membranes or intracellular compartments such as organelles, or in the cell's cytoplasm. Certain reactive groups allow the retention of the fluorophore in cells or organelles by reacting with cellular materials. In particular, haloalkyl- or halomethylbenzamide-substituted fluorophores are used to react selectively with intracellular components such as glutathione, or to retain the dye compounds within cells or within selected organelles where the dye compound is localized therein, according to methods previously described (U.S. Pat. No. 5,362,628 to Haugland et al, (1994); U.S. Pat. No. 5,576,424 to Mao et al. (1996) (in cells); and U.S. Pat. No. 5,459,268 to Haugland et al. (1995) and U.S. Pat. No. 5,686,261 to Zhang et al. (1997) (in mitochondria); all incorporated by reference). Polyfluoroaryl-substituted dye compounds are similarly retained in cells, in part by covalent attachment. The reactive dyes are used to localize staining in a part of the sample, e.g., where the localization of the corresponding functional group is indicative of a characteristic of the sample; or to retain the dye in a specific portion of the sample for extended periods of time, e.g., to follow the stained portion of the sample through a period of time or sequence of events. Alternatively, the reactive dyes are used according to this method to make dye-conjugates, as described above, that are separately useful for staining.

In an exemplary embodiment in which the dye solution comprises a dye-conjugate, the dye conjugate is a labeled member of a specific binding pair, and is used as a fluorescent probe for the complementary member of that specific binding pair, each specific binding pair member having an area on the surface or in a cavity which specifically binds to and is complementary with a particular spatial and polar organization of the other. The fluorescent conjugate of a specific binding pair member is useful for detecting and optionally quantifying the presence of the complementary specific binding pair member in a sample, by methods that are well known in the art. Optionally, the complementary binding pair member is present in a animal cell, plant cell, bacteria, yeast or virus. Alternatively, the complementary member is immobilized on a solid or semi-solid surface, such as a polymer, polymeric membrane or polymeric particle (such as a polymeric bead). The dye-conjugate may also comprise a dye in a blocked form wherein the block is later removed by the action of an enzyme or light.

Representative specific binding pairs are shown in Table 2. Typically a specific binding pair member conjugated to the dye is a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. The reactive dyes are used according to methods extensively known in the art, to prepare antibody conjugates for use in microscopy and immunofluorescent assays and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al., and a wide variety of other applications. Nucleotide conjugates are readily incorporated by DNA polymerase and can be used for in situ hybridization or other techniques.

In another preferred embodiment, the dyes of the invention are utilized as a component of one or more probes used in a multiplex assay for detecting one or more species in a mixture. As used herein, the term "multiplex assay" refers to an assay in which fluorescence from two or more dyes is detected, or in which fluorescence energy transfer between two or more dyes and one or more quencher is detected.

Probes that include a dye of the invention are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses generally meet at least two criteria: the fluorescent species is bright and spectrally well resolved; and the background fluorescence of the first dye does not significantly overlap the emission range of the second dye.

Thus, in a further embodiment, the invention provides a mixture comprising at least a first and a second dye of the invention. The first and second dyes are preferably conjugated to a component of a conjugate. The dyes may be conjugated to the same component or to different components.

The dyes of the invention allow for the design of multiplex assays in which more than one dye structure is used in the assay. A number of different multiplex assays using the dyes of the invention will be apparent to one of skill in the art. In one exemplary assay, each of the at least two distinct dyes are detected. Alternatively, an assay can be practiced in which each distinct dye moiety transfers energy to a distinct quencher to which the dye is "matched." The fluorophores can be bound to the same molecule as the quencher or to a different molecule. Moreover, similar to the dyes and the quenchers, the component of the different conjugates of use in a particular assay system can be the same or different.

In addition to the mixtures described above, the present invention also provides a method for detecting or quantifying a particular molecular species. The method includes: (a) contacting the species with a mixture such as that described above; and (b) detecting a change in a fluorescent property of one or more component of the mixture, the molecular species or a combination thereof, thereby detecting or quantifying the molecular species.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products.

The dyes of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

The compounds of the invention are also of use in the numerous fluorescence polarization assays that use conjugates of fluorescent dyes to low molecular weight drugs and ligands, which will be improved by the use of the dye compounds of the invention, e.g., U.S. Pat. Nos. 4,420,568 to Wang (1983) and 4,510,251 to Kirkemo et al. (1985).

In those embodiments in which a dye is conjugated to a specific binding pair member that is a chelator of calcium, sodium, magnesium, potassium, or other biologically important metal ion, the dye-conjugate functions as an indicator of the ion, which indicators are optionally further conjugated to a biological or plastic polymer according to methods known in the art; e.g., using analogs of the compounds described in U.S. Pat. Nos. 5,453,517 to Kuhn, et al. (1995); 5,405,975 to Kuhn, et al. (1995). Alternatively, the dye itself acts as a pH indicator at pH values within about 1.5 pH units of the individual dye's pKa. Typically the detectable optical response of the ion indicators is a change in fluorescence.

In another exemplary embodiment, the dye compounds are substrates for oxidative enzymes and other reactive oxidizing agents, particularly for peroxidase enzymes.

The enzyme substrates optionally contain additional substituents that provide additional advantages. For example, fluorophores modified to contain a lipophilic tail according to the synthesis described in U.S. Pat. No. 5,208,148 to Haugland et al. (1993), are useful for permeabilizing substrates for intracellular enzymes.

In another exemplary embodiment of the invention, the compounds are used to determine the efficiency of a cellular efflux pump of cells in a sample. Preferably the dye compounds are diacetates or diphosphates. The dye compound is used in the minimum concentration that gives a detectable fluorescence emission. Once the diacetate compounds are inside the cell, the blocking acetates are cleaved and the compound becomes highly fluorescent. The efficiency of the cellular efflux pump of cells in the sample is determined by comparing the fluorescence emission of cells in the sample with the fluorescence of cells having known efflux efficiency. Where the efflux pump is impaired, inhibited, or absent, the fluorescent compound is well retained in the cell; where the efflux pump is present and functioning, the fluorescence of the cells decreases markedly. The photostability of the present compounds is advantageous for monitoring the time course of fluorescence.

Another application where the enhanced photostability of the present dye compounds is particularly advantageous is use of the dye compounds for tracing. One or more dyes conjugated to a biologically compatible polymer, including amino acid polymers (typically proteins, including fluorescent proteins), carbohydrate polymers (typically dextrans), and polymeric microspheres (typically polystyrene) are readily prepared for use as tracers according to methods known in the art.

The dye compounds are advantageously used to stain biological samples, i.e. samples that comprise biological components. In one embodiment of the invention, the sample comprises heterogeneous mixtures of components, including intact cells, cell extracts, bacteria, viruses, organelles, and mixtures thereof. In another aspect of the invention, the sample comprises a single component or homogeneous group of components, e.g. biological polymers such as amino acid polymers, nucleic acid polymers or carbohydrate polymers, or lipid membrane complexes, whether the polymers are synthetic or natural.

The sample is typically stained by passive means, i.e., by incubation with the dye solution. Any other method of introducing the dye into the sample, such as microinjection of a dye solution into a cell or organelle, can be used to accelerate introduction of the dye into the sample. The dyes of the present invention are generally non-toxic to living cells and other biological components, within the concentrations of use.

The sample can be observed immediately after staining. The sample is optionally combined with other solutions in the course of staining, including wash solutions, permeabilization and/or fixation solutions, and other solutions containing additional detection reagents. Washing following staining generally improves the detection of the optical response due to the decrease in non-specific background fluorescence after washing. Satisfactory visualization is possible without washing by using lower labeling concentrations. A number of fixatives and fixation conditions suitable for practicing this invention are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the dyes described above are well retained in cells, and sample cells stained with these dyes retain considerable fluorescent staining after fixation. Fixation is optionally followed or accompanied by permeabilization, such as with acetone, ethanol, DMSO or various detergents, to allow bulky dye compounds, including dye-conjugates described above, to cross cell membranes, according to methods generally known in the art. The staining of the present invention is optionally combined with the use of an additional detection reagent that produces a detectable response due to the presence of a specific cell component, intracellular substance, or cellular condition, according to methods generally known in the art. Where the additional detection reagent has spectral properties that differ from those of the subject dye compounds, multicolor applications are possible.

The compounds of the invention are also of use to derivative low molecular weight compounds for their analysis by capillary zone electrophoresis (CZE), HPLC or other separation techniques.

Illumination

At any time after or during an assay or staining procedure, the sample is illuminated with a wavelength of light that results in a detectable optical response, and observed with a means for detecting the optical response. While the dye compounds are detectable calorimetrically, using ambient light, typically the dye compounds are detected by the fluorescence properties of the parent fluorophore. Upon illumination, such as by an ultraviolet or visible wavelength emission lamp, an arc lamp, a laser, or even sunlight or ordinary room light, the dye compounds, including dye compounds bound to the complementary specific binding pair member, display intense visible absorption as well as fluorescence emission. Selected equipment that is useful for illuminating the dye-conjugates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the dye compound and a second fluorophore with detectably different optical properties, typically by distinguishing the fluorescence response of the dye-conjugate from that of the second fluorophore. Where the sample is examined using a flow cytometer, examination of the sample optionally includes isolation of particles within the sample based on the fluorescence response of the dye compound by using a sorting device.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or x-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample. The presence or absence of the optical response after the elapsed time is indicative of one or more characteristic of the sample. Comparison of the degree of staining with a standard or expected response can be used to determine whether and to what degree the sample possesses a given characteristic.

Sample Preparation

The end user will determine the choice of the sample and the way in which the sample is prepared. The sample includes, without limitation, any biological derived material or aqueous solution. The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons.

When the compounds of the invention are used as components of an assay system for a target species in a mixture, such as an enzyme, the target concentration is conveniently in the range of about 1 nM to 500 nM, more usually in the range of about 25 to 250 nM. One may use an individual compound of the invention, multiple compounds of the invention or a combination of a compound of the invention and a fluorophore or quencher of a different structure in order to detect the presence of or determine the characteristics of a target in a sample.

When the components of the invention are species that bind to targets that are specific biological structures (e.g., enzymes, receptors, ligands, antigens, antibodies, etc.), the reaction time between the compound or conjugate of the invention and the target will usually be at least about 5 min, more usually at least about 30 min and preferably not more than about 180 min, preferably not more than about 120 min, depending upon the temperature, concentrations of enzyme and substrate, etc. By using a specific time period for the reaction or taking aliquots at 2 different times, the rate of reaction can be determined for comparison with other determinations. The temperature will generally be in the range of about 20 to 50° C., more usually in the range of about 25 to 40° C.

If the assay focuses on an enzyme, coenzyme, if any, is preferably present in excess, so as not be rate limiting. Generally, with the concentrations of enzyme indicated above, the concentration of coenzyme will be at least about 0.1 mM, usually at least about 1 mM and not more than about 25 mM. The coenzyme solution should be prepared freshly for each series of determinations.

Various buffers can be used in the assays of the invention. These buffers include PBS, Tris, MOPS, HEPES, phosphate, etc. The pH will vary depending upon the particular assay system, generally within a readily determinable range wherein one or more of the sulfonic acid moieties is deprotonated. The concentration of buffer is generally in the range of about 0.1 to 50 mM, more usually 0.5 to 20 mM.

In certain instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

After sufficient time for a detectable amount of product to form, the reaction is optionally quenched. Various quenching agents may be used, both physical and chemical. Conveniently, a small amount of a water-soluble inhibitor may be added, such as acetonitrile, DMSO, SDS, methanol, DMF, etc. The amount of inhibitor will vary with the nature of the inhibitor and may be determined empirically.

Kits

In another aspect, the present invention provides kits that include a fluorescent compound of the invention. The kit will generally also include instructions for using the compound of the invention in one or more methods.

In an exemplary embodiment, the kit includes a reactive compound of the invention and instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

In another exemplary kit of the invention, the instructions provided are for performing an assay that detects oxidative or reductive agents or conditions in a sample. For example, in one embodiment, directions are provided for detecting a reactive oxygen species, or an enzyme, organism, or other agent that generates a reactive oxygen species in a sample.

A detailed description of the invention having been provided above, the following examples are given for the purpose of illustrating the invention and shall not be construed as being a limitation on the scope of the invention or claims.

EXAMPLES

Example 1

To a solution of 1,3,6-tris-sulfo-8-pyrenyloxyacetic acid, trisodium salt (2.19 g, 3.76 mmol) in E-pure water (200 mL) was added DOWEX-50W triethylammonium form (25 g) and the mixture was stirred at room temperature for 20 min. DOWEX-50W was filtered off and washed with E-pure water. The filtrate was concentrated and lyophilized.

The residue was dissolved in anhydrous DMA (100 mL), DCC (2.3 g, 11.28 mmol) and HOSu (432 mg, 3.76 mmol) were added and the mixture was stirred for 2 h at room temperature. Ethyl isonipecotate (1.77 g, 11.28 mmol) was added and the mixture was kept stirring at room temperature for 3 days. Precipitate (DCU) was filtered off and washed with MeOH. The filtrate was concentrated to ca 10 ml and EtOAc (200 mL) was added. The precipitate was collected and washed with EtOAc. The precipitate was redissolved in MeOH/H$_2$O (1:1, 150 mL), undissolved precipitate (DCU) was filtered off and washed with water. The filtrate was concentrated to give crude compound 1.

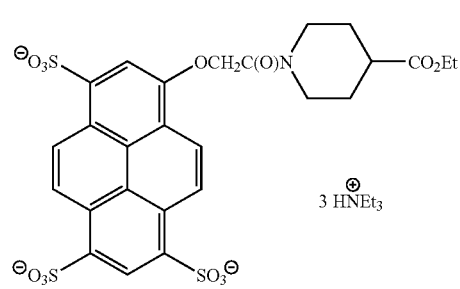

Example 2

To a solution of crude 1 in water (150 mL) was added LiOH (430 mg, 17.9 mmol) and the mixture was stirred at room temperature overnight. The reaction mixture was neutralized to pH=7 with 10% HCl, and then concentrated and lyophilized. The crude product was purified by HPLC to give compound 2 as

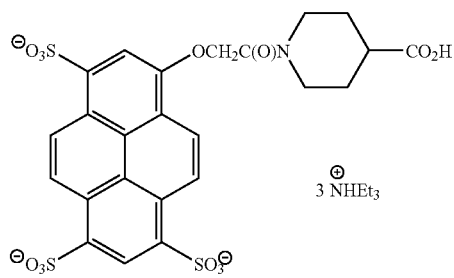

2

Example 3

To 2 (34 mg, 0.033 mmol) in anhydrous DMA (6 mL) were added DSC (44 mg, 0.172 mmol) and DMAP (2 mg, 0.0164 mmol) and the mixture was stirred at room temperature for 1 h. The reaction mixture was concentrated in vacuo to ca 2 mL. EtOAc (20 mL) was added and the precipitate was collected. The precipitate was washed with EtOAc and redissolved in anhydrous DMA (1 mL) that was diluted with CH$_3$CN (5 mL). EtOAc (30 mL) was added and the precipitate was collected. The precipitate was washed with EtOAc and ether and then dried under vacuum to yield compound 3 (30 mg).

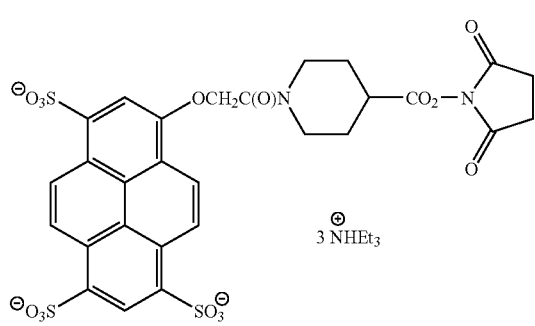

3

Example 4

To 3 (20 mg, 0.02 mmol) in dry DMF (2 mL) at 5° C. was added a solution of 6-aminohexanoic acid (3 mg, 0.023 mmol) and triethylamine (1 drop) in H$_2$O (1 mL). The mixture was stirred at 5° C. for 30 minutes and then concentrated to dryness in vacuo. The residue was purified by reverse phase HPLC to give 4 (15 mg).

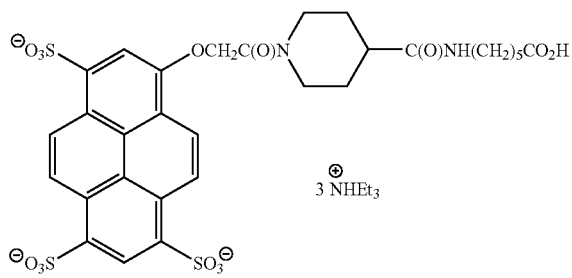

4

Example 5

To 2 (100 mg, 0.11 mmol) in dry DMF (5 mL) at 0° C. was added Et$_3$N (44 µL, 0.33 mmol) and 2,3,5,6-tetrafluorophenyl trifluoroacetate (53 mg, 0.22 mmol). The mixture was stirred at 0° C. for 1 hr and then concentrated to dryness in vacuo. The residue was purified by column chromatography on silica gel using CH$_3$CN:H$_2$O=8.5:1.5 as eluent to give 5 (76 mg).

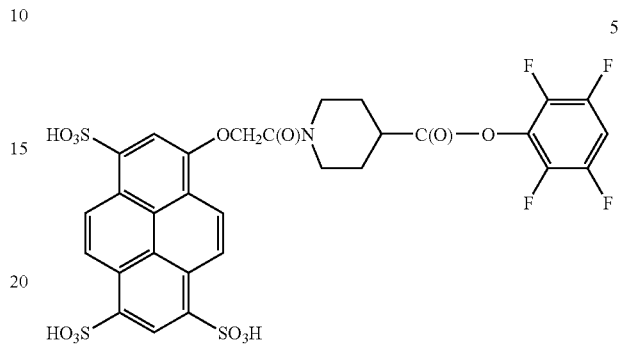

5

Example 6

To 1,3,6-tris-sulfo-8-pyrenyloxyacetic acid, triethylammonium salt (100 mg, 0.12 mmol) in anhydrous DMA was added DCC (30 mg, 0.15 mmol) and N-hydroxysuccinimide (14 mg, 0.12 mmol). The mixture was stirred at room temperature for 2 hrs. A solution of cis-4-amino-1-cyclohexanecarboxylic acid (19 mg, 0.13 mmol) and triethylamine (2 drops) in H$_2$O was added and the mixture was stirred at room temperature overnight. The mixture was concentrated to dryness in vacuo and the residue was purified by reverse phase HPLC to give 6 (65 mg).

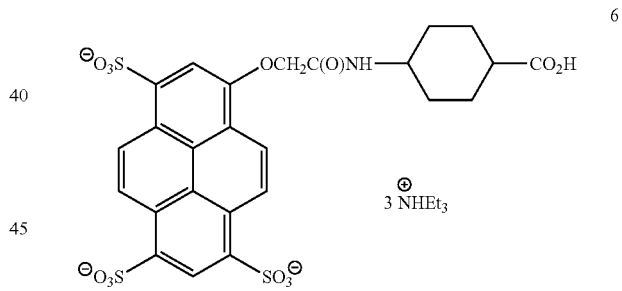

6

Example 7

Compound 7 was prepared according to the method to synthesis compound 6 from 5-amino-1,3-cyclohexadiene-1-carboxylic acid hydrochloride.

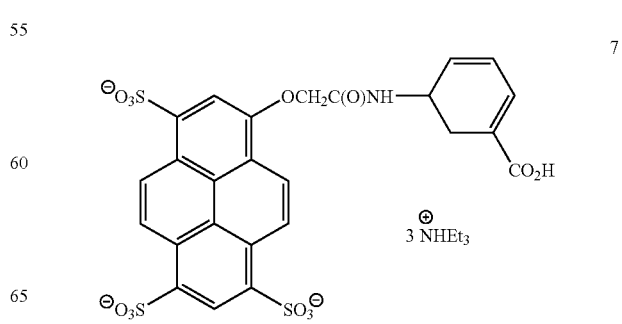

7

Example 8

Compound 8 was prepared according to the method to synthesize compound 6 from 3-carboxypyrrolidine.

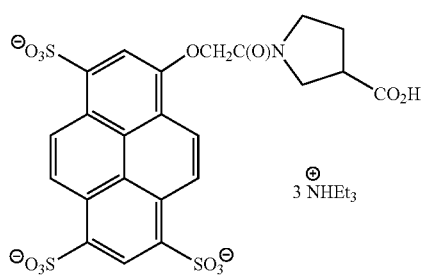

Example 9

Compound 9 was prepared according to the method to synthesize compound 6 from 3-amino-1-cyclopentanecarboxylic acid.

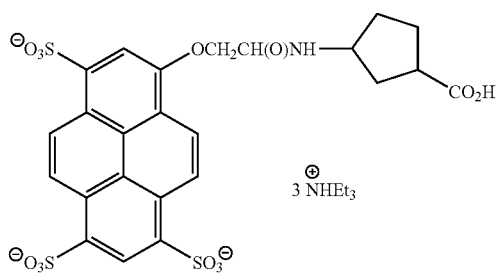

Example 10

To 1,3,6-tris-sulfo-8-pyrenyloxyacetic acid, triethylammonium salt (100 mg, 0.12 mmol) in anhydrous DMA was added DCC (30 mg, 0.15 mmol) and N-hydroxysuccinimide (14 mg, 0.12 mmol). The mixture was stirred at room temperature for 2 hrs. A solution of 3-tert-butoxycarbonylaminopiperidine (27 mg, 0.13 mmol) and triethylamine (2 drops) in DMF (1 mL) was added and the mixture was stirred at room temperature overnight. The mixture was concentrated to dryness in vacuo and the residue was purified by reverse phase HPLC to give 10 (72 mg).

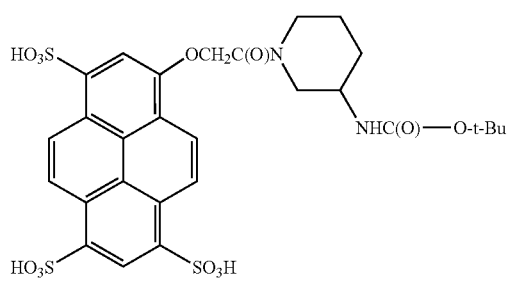

Example 11

To trifluoroacetic acid (1 mL) at 0° C. was added 10 (20 mg). The mixture was stirred at 0° C. for 30 minutes and then added to EtOAc (10 mL). The precipitate was collected by centrifuge and dried to constant weight under vacuum to give 11 (13 mg).

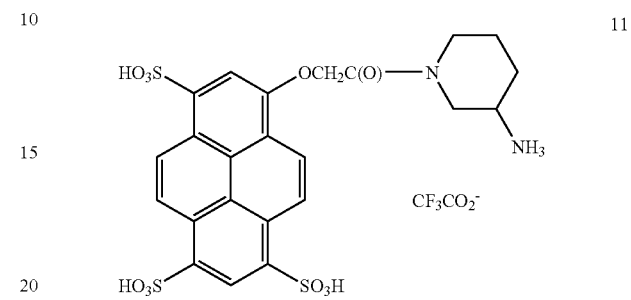

Example 12

To 1,3,6-trisulfo-8-pyrenyloxyacetic acid, trisodium salt (150 mg, 0.25 mmol) in E-pure water (20 mL) was added DOWEX-50W triethylammonium form (3 g) and the mixture was stirred at room temperature for 20 min. DOWEX-50W was filtered off and washed with E-pure water. The filtrate was concentrated and lyophilized. The residue was dissolved in anhydrous DMA (20 mL), DCC (155 mg, 0.75 mmol) and HOSu (58 mg, 0.5 mmol) were added and the mixture was stirred at room temperature for 3 days. A clear solution of 4-(methylamino)butyric acid hydrochloride (115 mg, 0.75 mmol), tert-butyldimethylsilyl chloride (113 mg, 0.75 mmol) and triethylamine (1.0 mL) in anhydrous $CH_2Cl_2$ (10 mL) was added to the above reaction mixture and stirred at room temperature overnight. The reaction mixture was concentrated to ca. 1 mL and water (15 mL) was added. To the solution, LiOH (150 mg, 6.25 mmol) was added and stirred at room temperature overnight. Precipitate (DCU) was filtered off and washed with water. The filtrate was concentrated and purified by preparative HPLC to give compound 12 (97 mg).

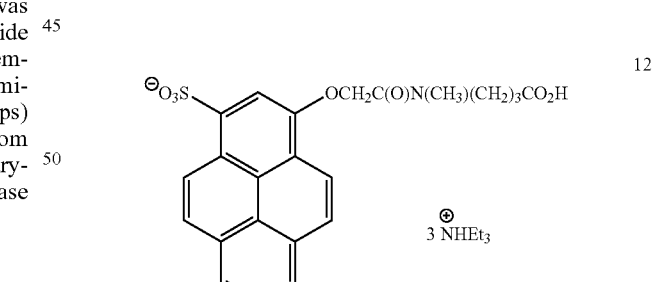

Example 13

To compound 12 (97 mg, 0.095 mmol) in anhydrous DMA (6 mL) was added DSC (73 mg, 0.285 mmol) and DMAP (3 mg, 0.0246 mmol). The mixture was stirred at room temperature for 1 h. The reaction mixture was concentrated to ca 2 mL. EtOAc (20 mL) was added and the precipitate was collected and washed with EtOAc. The precipitate was redissolved in anhydrous DMA (1 mL) and diluted with $CH_3CN$ (5 mL). EtOAc (30 mL) was added and precipitate was collected. The precipitate was washed with EtOAc, ether and then dried under vacuum to yield compound 13 (85 mg).

temperature for 2 hrs and then concentrated to dryness in vacuo. The residue was purified by column chromatography on silica gel using $CH_3CN/H_2O$ as eluent to give 15 (50 mg).

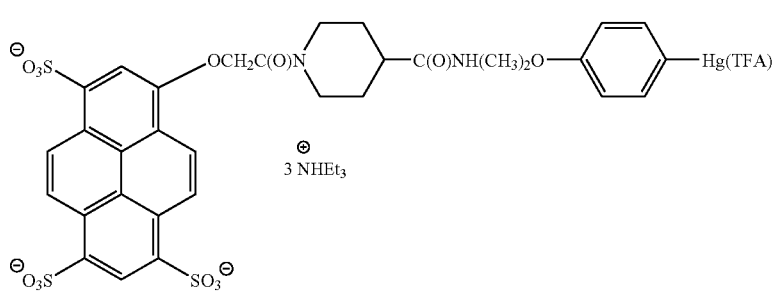

15

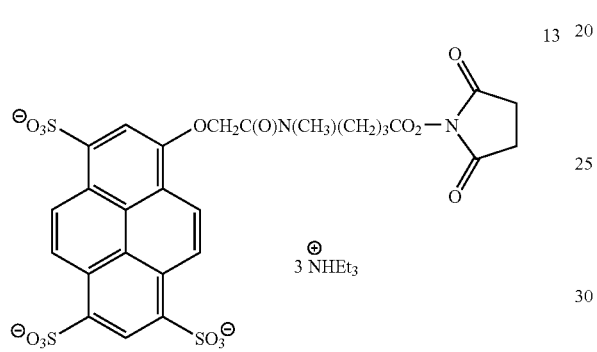

13

Example 14

To a solution of 3 (300 mg, 0.29 mmol) in dry DMA (10 mL) at 0° C. was added $Et_3N$ (0.162 mL, 1.16 mmol) and N-(5-aminopentyl)maleimide, trifluoroacetate salt (112 mg, 0.37 mmol). The mixture was stirred at 0° C. for 1 h and concentrated to dryness in vacuo. The residue was purified by reverse phase HPLC to give 14 (30 mg).

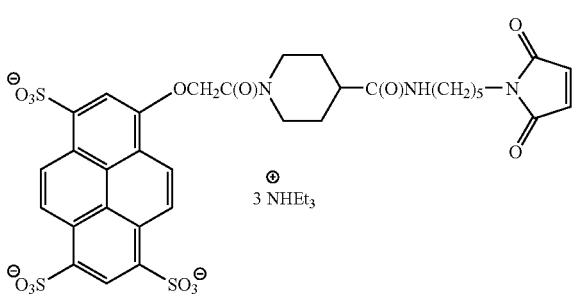

14

Example 15

To a solution of 3 (200 mg, 0.19 mmol) and $Et_3N$ (0.108 mL, 0.76 mmol) in DMA (20 mL) was added a solution of 4-(2-aminoethoxy)phenylmercuric trifluoroacetate trifluoroacetate (88 mg, 0.19 mmol). The mixture was stirred at room

Example 16

Reaction of Goat Anti-Mouse IgG (GAM) with the NHS-Ester of 4

A solution of GAM (8 mg/mL in 10 mM potassium phosphate, 150 mM sodium chloride; 0.25 mL, 2 mg) was measured into test tubes and the pH was adjusted to 8.0 with 1 M sodium bicarbonate (pH 8.3) (25 μL). The resulting GAM solution was reacted with a 10-, 15- or 25-molar excess of the NHS-ester of 4 as a solution in E-Pure water (10 mg/mL) for 1 h at room temperature. The dye-protein conjugates were separated from free dye by size-exclusion chromatography using three columns (0.75×20 cm) of BioRad BioGel P-30 (fine) eluted with PBS. The initial protein-containing band was collected from each of the three columns.

Figure 2:
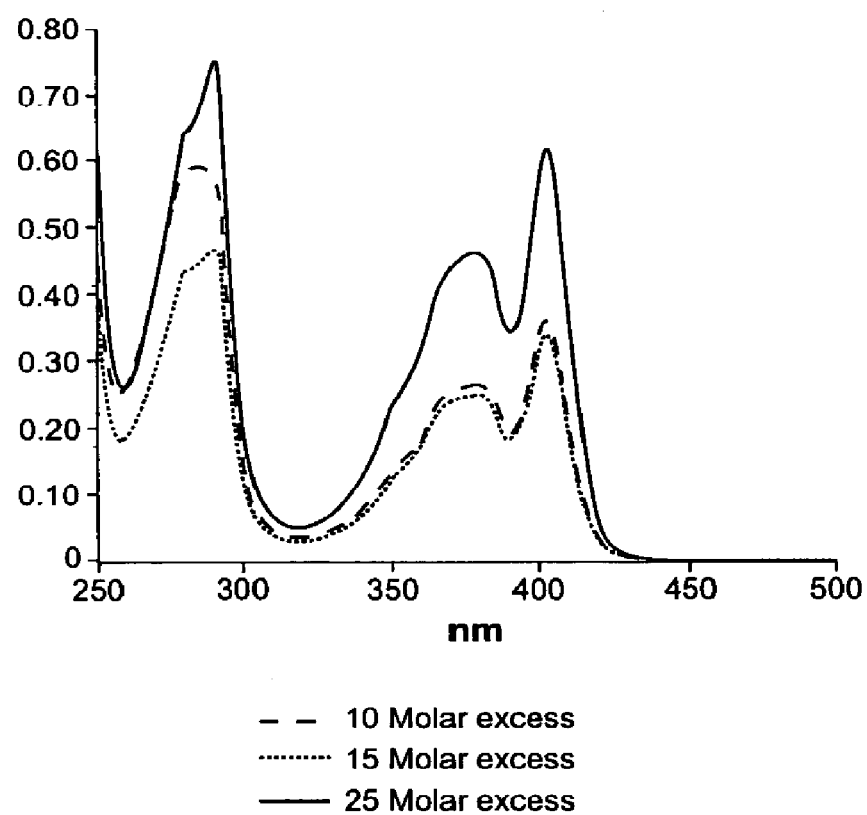
FIG. 2 is a UV/Vis spectrum of compound 4.

Absorbance spectra are collected on any appropriate instrument, e.g., a Perkin-Elmer Lambda 35 UV/Vis spectrometer (FIG. 2). FIG. 2 is the UV/Vis spectrum of 4.

Figure 3:
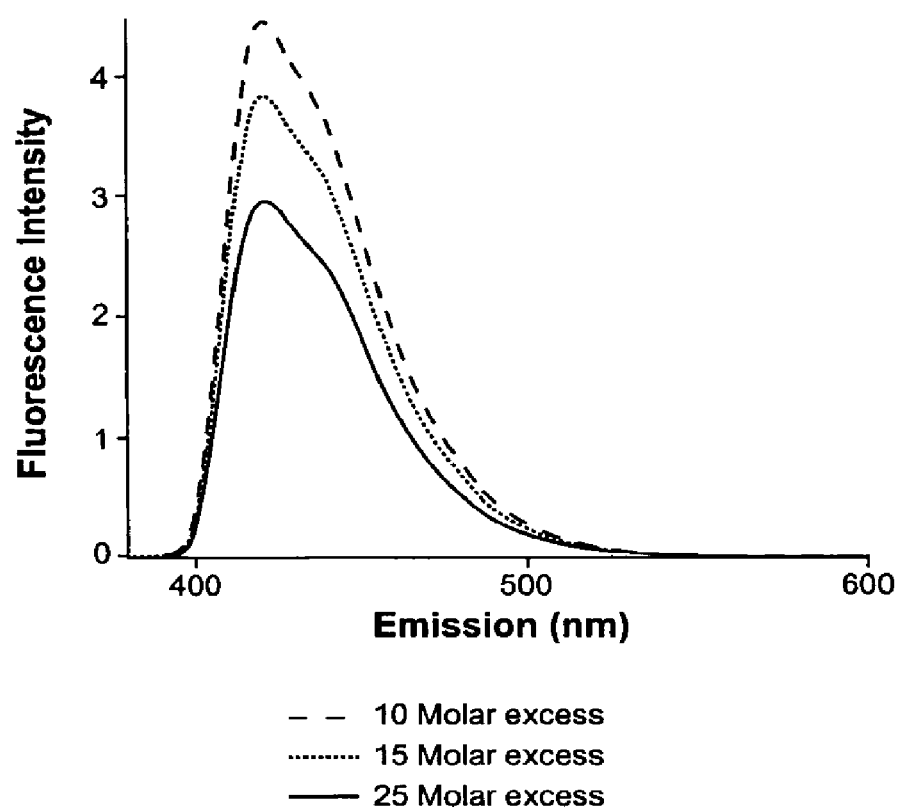
FIG. 3 is a fluorescence emission spectrum of compound 4.

The fluorescence emission spectra are obtained on any of a variety of art-recognized fluorescent spectrometers, e.g., Aminco Bowman Series W Luminescence Spectrometer, excited at 375 nm (FIG. 3). FIG. 3 is the fluorescence emission spectrum of 4.

The preceding examples can be repeated with similar success by substituting the specifically described fluorescent compounds of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having the formula:

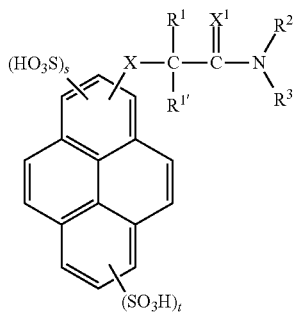

wherein
- $R^1$ and $R^{1'}$ are each H;
- X and $X^1$ are each O;
- s and t are independently selected from the integers from 0 to 3, with the proviso that at least one of s and t is at least 1;
- $R^2$ is a member selected from substituted or unsubstituted alkyl, substituted or unsubstituted cycloalkyl, substituted or unsubstituted heteroalkyl and substituted or unsubstituted heterocycloalkyl;
- $R^3$ is a member selected from substituted or unsubstituted alkyl, substituted or unsubstituted heteroalkyl, substituted or unsubstituted cycloalkyl, and substituted or unsubstituted heterocycloalkyl; and
- $R^2$ and $R^3$, together with the nitrogen to which they are bound are joined to form a ring which is substituted with a reactive group, wherein said reactive group is a member selected from an acrylamide, an activated ester of a carboxylic acid, an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine a hydrazide, an imido ester, an isocyanate, an isothiocyanate, a maleimide, a phosphoramidite, a reactive platinum complex, a sulfonyl halide, a thiol group, and a photoactivatable group.

2. The compound according to claim 1, wherein s is 1; and t is 2.

3. The compound according to claim 1, having the formula:

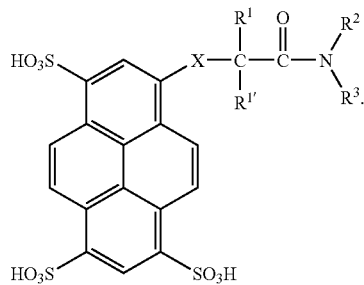

* * * * *

UNITED STATES PATENT AND TRADEMARK OFFICE
CERTIFICATE OF CORRECTION

PATENT NO. : 8,039,642 B2
APPLICATION NO. : 11/871596
DATED : October 18, 2011
INVENTOR(S) : Liu et al.

Page 1 of 1

It is certified that error appears in the above-identified patent and that said Letters Patent is hereby corrected as shown below:

Column 44, Claim 1, line 9, insert a --,-- immediately after the term "hydrazine".

Signed and Sealed this
Third Day of January, 2012

David J. Kappos
*Director of the United States Patent and Trademark Office*